(12) United States Patent
Donovan et al.

(10) Patent No.: US 7,357,934 B2
(45) Date of Patent: Apr. 15, 2008

(54) INTRACRANIAL BOTULINUM TOXIN THERAPY FOR FOCAL EPILEPSY

(75) Inventors: Stephen Donovan, Capistrano Beach, CA (US); Joseph Francis, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 387 days.

(21) Appl. No.: 10/421,504

(22) Filed: Apr. 22, 2003

(65) Prior Publication Data

US 2003/0202990 A1    Oct. 30, 2003

Related U.S. Application Data

(60) Continuation-in-part of application No. 09/903,849, filed on Jul. 12, 2001, now abandoned, which is a division of application No. 09/596,306, filed on Jun. 14, 2000, now Pat. No. 6,306,403.

(51) Int. Cl.
*A61K 39/08*    (2006.01)
*A61K 38/16*    (2006.01)

(52) U.S. Cl. ...................... 424/239.1; 514/12

(58) Field of Classification Search ...................... None
See application file for complete search history.

(56) References Cited

U.S. PATENT DOCUMENTS

| | | | |
|---|---|---|---|
| 4,883,666 A * | 11/1989 | Sabel et al. ............... | 424/422 |
| 5,427,291 A | 6/1995 | Smith | |
| 5,674,205 A | 10/1997 | Pasricha et al. | |
| 5,766,605 A | 6/1998 | Sanders et al. | |
| 5,989,545 A | 11/1999 | Foster et al. | |
| 6,063,768 A | 5/2000 | First | |
| 6,113,915 A | 9/2000 | Aoki et al. | |
| 6,306,423 B1 | 10/2001 | Donovan et al. | |
| 6,365,164 B1 | 4/2002 | Schmidt | |

FOREIGN PATENT DOCUMENTS

| | | |
|---|---|---|
| DE | EP0 605 501 B1 | 9/1992 |
| WO | WO 95/17904 | 7/1995 |

OTHER PUBLICATIONS

Merck Manual, Second Home Edition, Chapter 85, online version accessed Aug. 10, 2005.*
Physician's Desk Reference, electronic version, entry for botulinum toxin BOTOX accessed Feb. 25, 2005.*
Korolkiewicz 1998. Pharmacological Research 37:477-483.*
Rabasseda 1998. Toxincon. 26:329-336.*
Smith 1993. Epilepsia 34:43-53.*
Jitpimolmard et al. 1998. J Neurol Neurosurg Psychiatry 64:751-757.*
Scremin et al. 1998. Brain Research Bulletin 45:167-174.*
Danober 1995. Neuroscience 69:1183-1193.*
Bhattacharya et al. 2000, Movement Disorders 15, supplement 2:51-52.*
Whittington 1994. Journal of Phsyiology 481.3:593-604.*
De Deyn 1992. Epilepsy Research 12:87-110, particularly pp. 97-98.*
Hagemann 1999. Brain Research 818:127-134.*
Aguilera, Jose et al., Stereotaxic Injection of Tetanus toxin in Rat Central Nervous System Causes Alteration in Normal Levels of Monoamines; *Journal of Neurochemistry*; vol. 56, No. 3, 1991, pp. 733-738.
Barnes, Deborah M.; Debate About Epilepsy: What Initiates Seizures?; *Science*; vol. 234, Nov. 21, 1986, pp. 938-941.
Bejjani, Boulos-Paul et al.; Bilateral subthalamic stimulation for Parkinson's disease by using three-dimensional stereotactic magnetic resonance imaging and electrophysiological guidance; *J. Neurosurg*; vol. 92, Apr. 2000, pp. 615-625.
Bellezza, David M. et al.; Stereotactic Interstitial Brachytherapy; *Textbook of Stereotactic and Functional Neurosurgery*; Edited by Gildenberg et al.; McGraw-Hill Publ.; Chapter 66, pp. 577-580, 1997.
Benabid, Alim L. et al.; Deep brain stimulation of the corpus luysi (subthalamic nucleus) and other targets in Parkinson's disease. Extension to new indications such as dystonia and epilepsy; *J Nuerol*; 2001, 248, Suup 3, pp. 111/37-111/47.
Bergquist, Filip et al.; Evidence for different exocytosis pathways in dendritic and terminal dopamine release in vivo; *Brain Research*; 950, 2002, pp. 245-253.
Bigalke, Hans et al.; Botulinum A Neurotoxin Inhibits Non-Cholinergic Synaptic Transmission in Mouse Spinal Cord Neurons in Culture; *Brain Research*; 360, 1985, pp. 318-324.
Bigalke, Hans et al.; Tetanus Toxin and Botulinum A Toxin Inhibit Release and Uptake of Various Transmitters, as Studied with Particulate Preparations from Rat Brain and Spinal Cord; *Naunyn-Schmiedeberg's Arch Pharmacol*; 1981, 316, pp. 244-251.
Billet, Sara et al.; Cholinergic projections to the visual thalamus and superior colliculus; *Brain Research*; 847, 1999, pp. 121-123.
Binz, Thomas et al.; The Complete Sequence of Botulinum Neurotoxin Type A and Comparison with Other Clostridial Neurotoxins; *J Biochem (Tokyo)*; Jun. 1990, 5, 265 (16), pp. 9153-9158.
Boyd, R.S. et al.; The effect of botulinum neurotoxin-B on insulin release from a β-cell line and Boyd R.S. et al.; The insulin secreting β-cell line, HIT-15, contains SNAP-25 which is a target for botulinum neurotoxin-A; both published at *Movement Disorders*; vol. 10, No. 3, 1995, pp. 376.
Brem, Henry et al.; Placebo-controlled trial of safety and efficacy of intraoperative controlled delivery by biodegradable polymers of chemotherapy for recurrent gliomas; *The Lancet*; vol. 345, Apr. 22, 1995, pp. 1008-1012.
Brem, Henry et al.; The safety of interstitial chemotherapy with BCNU-loaded polymer followed by radiation therapy in the treatment of newly diagnosed malignant gliomas: phase I trial; *Journal of Neuro-Oncology*; 26, 1995, pp. 111-123.

(Continued)

*Primary Examiner*—Robert C. Hayes
*Assistant Examiner*—Daniel E Kolker
(74) *Attorney, Agent, or Firm*—Claude L. Nassif; Stephen Donovan

(57) ABSTRACT

Methods for treating and/or curing epilepsy by intracranial administration of a botulinum toxin.

19 Claims, 4 Drawing Sheets

OTHER PUBLICATIONS

Brophy, B.P. et al.; Thalamotomy for Parkinsonian Tremor; *Stereotactic and Functional Neurosurgery*; 1997, 69, pp. 1-4.

Cmelak, Anthony J. et al.; Low-dose stereotactic radiosurgery is inadequate for medically intractable mesial temporal lobe epilepsy: a case report; *Seizure*; 2001, 10, pp. 442-446.

Dichter, Marc A.; Basic Mechanisms of Epilepsy: Targets for Therapeutic Intervention; *Epilepsia*; vol. 38, Suppl. 9, 1997, pp. S2-S6.

Dykstra, Dennis D. et al.; Treatment of Detrusor-Sphincter Dyssynergia with Botulinum A Toxin: A Double-Blind Study; *Arch Phys Med Rehabil*; Jan. 1990, 71, pp. 24-26.

Fauci et al; *Harrison's Principles of Internal Medicine* 14th Edition; Published by McGraw-Hill, pp. 2321, 1998.

Fried, Itzhak et al.; Cerebral microdialysis combined with single-neuron and electroencephalographic recording in neurosurgical patients; *J Neurosurg*; 91, 1999, pp. 697-705.

Fung, Lawrence K. et al.; Pharmacokinetics of Interstitial Delivery of Carmustine, 4-Hydroperoxycyclophosphamide, and Paclitaxel from a Biodegradable Polymer Implant in the Monkey Brain; *Cancer Research*; 58, Feb. 15, 1998, pp. 672-684.

Galarreta, Mario et al.; Frequency-dependent synaptic depression and the balance of excitation and inhibition in the neocortex; *Nature Neuroscience*; vol. 1 No. 7, Nov. 1998, pp. 587-594.

Gale, Karen; Focal trigger zones and pathways of propagation in seizure generation; *Epilepsy: models, mechanism and concepts*; Schwartzkroin, P.A. Editor, Cambridge U. Press, U.K. 1993, pp. 48-93.

Ganguly, Karunesh et al.; Enhancement of presynaptic neuronal excitability by correlated presynaptic and postsynaptic spiking; *Nature Neuroscience*; vol. 3 No. 10, Oct. 2000, pp. 1018-1026.

Gaspar, Laurie E. et al.; Permanent 125 Iodine Implants for Recurrent Malignant Gliomas; *Int. J. Radiation Oncology Biol. Phys.*; 1999, vol. 43, No. 5, pp. 977-982.

Goddard, Graham V.; A Permanent Change in Brain Function Resulting from Daily electrical Stimulation; *Expermental Neurology*; 25, 1969, pp. 295-330.

Gonelle-Gispert, Carmen et al.; SNAP-25a and -25b isoforms are both expressed in insulin-secreting cells and can function in insulin secretion; *Biochem J.*; 1999, 339, pp. 159-165.

Habermann, E.; I-Labeled Neurotoxin from Clostridium Botulinum A: Preparation, Binding to Synaptosomes and Ascent to the Spinal Cord; *Naunyn-Schmiedeberg's Arch. Pharmacol*; 281, 1974, pp. 47-56.

Habermann, E; Inhibition by tetanus and botulinum A toxin of the release of [3 H] noradrenaline and [3 H] GABA from rat brain homogenate; *Experientia*; 44, 1988 pp. 224-226.

Habermann, E. et al.; Tetanus Toxin and Botulinum A and C Neurotixins Inhibit Noradrenaline Release from Cultured Mouse Brain; *Journal of Neurochemistry*; vol. 51, No. 2, 1988, pp. 522-527.

Heikkinen, E.R. et al.; Stereotactic Radiotherapy Instead of Conventional Epilepsy Surgery; *Acta Neurochirurgica*; 1992, 1994, pp. 159-160.

Huttner, W.B. et al.; Exocytotic and endocytotic membrane traffic in neurons; *Current Opinion in Neurobiology*; 1991, 1, pp. 388-392.

Jankovic, Joseph et al. editors; *Therapy with Botulinum Toxin*; Marcel Dekker, Inc., publisher, pp. 5 and 150, 1994.

Jefferys, J.G.R. et al., Chronic focal epilepsy induced by intracerebral tetanus toxin; *The Italian Journal of Neurological Sciences*; 16, 1995, pp. 27-32.

Jellinger, K.A.; Post mortem studies in Parkinson's disease—is it possible to detect brain areas for specific symptoms?; *J Neural Transm*; 1999, Suppl 56, pp. 1-29.

Kaplitt, M.G. et al.; Surgical Drug Delivery for Neurodegenerative Diseases; Clinical Neurosurgery; vol. 48, Chp 10, pp. 127-144, Proceedings of the Congress of Neurological Surgeons, 2001, Published by Lippincott Williams & Wilkins.

Kohl, A. et al.; Comparison of the effect of botulinum toxin A (Botox®) with the highly-purified neurotoxin (NT 201) in the extensor digitorum brevis muscle test; *Movement Disorders*; 2000, 15, Suppl 3, 165, pp. 805.

Koller, W.C. et al.; Surgical treatment of Parkinson's disease; *Journal of the Neurological Sciences*; 167, 1999, pp. 1-10.

Kwan, P. et al.; Refractory epilepsy: a progressive, intractable but preventable condition?; *Seizure*; 2000, 11, pp. 77-84.

Lan, J. et al.; Activation of Metabotropic Glutamate Receptor 1 Accelerates NMDA Receptor Trafficking; *The Journal of Neuroscience*; Aug. 15, 2001, 21, (16), pp. 6058-6068.

Landi, A. et al.; Accuracy of Stereotactic Localisation with Magnetic Resonance Compared to CT Scan: Experimental Findings; *Acta Neurochir*; 2001, 143, pp. 593-601.

Levy, Ron et al.; Lidocaine and muscimol microinjections in subthalamic nucleus reverse parkinsonian symptoms; *Brain*; 2001, 124, pp. 2105-2118.

Lomber, Stephen G.; The advantages and limitations of permanent or reversible deactivation techniques in the assessment of nueral function; *Journal of Neuroscience Methods*; 86, 1999, pp. 109-117.

Lozano, Andres et al.; Methods for microelectrode-guided posteroventral pallidotomy; *J Neurosurg*; vol. 84, Feb. 1996, pp. 194-202.

Malpeli, Joseph; Reversible inactivation of subcortical sites by drug injection; *Journal of Neuroscience Methods*; 86, 1999, pp. 119-128.

Marjama-Lyons, Jill et al.; Tremor-Predominant Parkinson's Disease; Drugs & Aging; Apr. 16, 2000, (4), pp. 273-278.

Martin, J.H. et al.; Pharmacological inactivation in the analysis of the central control of movement; *Journal of Neuroscience Methods*; 86, 1999, pp. 145-159.

McCormick, David et al.; On The Cellular And Network Bases Of Epileptic Seizures; *Annual Rev Physiol*; 2001, 63, pp. 815-846.

Mellanby, Jane; Tetanus Toxin as a Tool for Investigating the Consequences of Excessive Neuronal Excitation; *Botulinum and Tetanus Neurotoxins*; edited by B.R. DasGupta, Plenum Press, 1993, pp. 291-297.

Morrell, Frank et al.; Multiple subpial transaction: a new approach to the surgical treatment of focal epilepsy; *J Neurosurg*; 70, 1989, pp. 231-239.

Moyer, Elizabeth et al.; Botulinum Toxin Type B: Experimental and Clinical Experience; *Therapy with Botulinum Toxin*; edited by Jankovic, J. et al., published by Marcel Dekker, Inc., Chp 6, pp. 71-85, 1994.

Mulligan, Lisa et al.; Multiple Subpial Transections: The Yale Experience; *Epilepsia*; 42(2), 2001, pp. 226-229.

Nadeau, Stephen E.; Parkinson's Disease; *J by the American Geriatrics Society*; 1997, 45, pp. 233-240.

Naumann, Markus et al.; Botulinum toxin type A in the treatment of focal, axillary and palmar hyperhidrosis and other hyperhidrotic conditions; European Journal of Neurology, 1999, 6, Suppl 4, S111-S115.

Nowinski, Wieslaw et al.; Computer-Aided Stereotactic Functional Neurosurgery Enhanced by the Use of the Multiple Brain Atlas Database; *IEEE Transactions on Medical Imaging*; V1 19, No. 1, Jan. 2000, pp. 62-69.

Oakman, S.A. et al.; Characterization of the Extent of Pontomesencephalic Cholinergic Neurons' Projections to the Thalamus: Comparison with Projections to Midbrain Dopaminergic Groups; *Neuroscience*, vol. 94, No. 2, 1999, pp. 529-547.

Owe-Larsson, Bjorn et al.; Distinct Effects of Clostridial Toxins on Activity-dependent Modulation of Autaptic Responses in Cultured Hippocampal Neurons; *European Journal of Neuroscience*, vol. 9, 1997, pp. 1773-1777.

Parrent, Andrew G.; Stereotactic radiofrequency ablation for the treatment of gelastic seizures associated with hypothalamic hamartoma; *J Neurosurg*, 91, 1999, pp. 881-884.

Parrent Andrew G. et al.; Stereotactic Surgery for Temporal Lobe Epilepsy; *The Canadian Journal of Neurological Sciences*, Suppl 1, pp. S79-S96, May 2000.

Parton, R.G. et al.; Cell Biology of Neuronal Endocytosis; *Journal of Neuroscience Research*, 1993, 36, pp. 1-9.

Pearce, Bruce et al.; Pharmacologic Characterization of Botulinum Toxin for Basic Science and Medicine; *Toxicon*; vol. 35, No. 9, 1997, pp. 1373-1412.

Penn, Richard D.; The Future of CNS Infusion Systems; *Textbook of Stereotactic and Functional Neurosurgery*; edited by Gildenberg et al., McGraw-Hill publishers, Chp 218, pp. 2073-207, 1997.

Perry, Elaine et al.; Acetylcholine in mind: a neurotransmitter correlate of consciousness?; *TINS*, 1999, vol. 22, No. 6, pp. 273-290.

Playfer, J.R.; Parkinson's disease; *Postgrad Med J*; 1997, 73, pp. 257-264.

Prince, David A.; Cellular Mechanisms of Interictal-ictal Transitions; *Mechanisms of Epileptogenesis The Transition to Seizure*; edited by Dichter, published by Plenum Press, Chp 4, pp. 57-71, 1988.

Prince, David A.; Epileptogenic Neurons and Circuits; *Jasper's Basic Mechanisms of the Epilepsies Third Edition: Advances in Neurology*; vol. 79, edited by Delgado-Escueta et al., 1999, Chp 45, pp. 665-684.

Racine, Ronald J.; Modification of Seizure Activity by Electrical Stimulation: I. After-Discharge Threshold; *Electroenceph clin Neurophysiol*; 1972, 32, pp. 269-279.

Racine, Ronald J.; Modification of Seizure Activity by Electrical Stimulation: II. Motor Seizure; *Electroenceph clin Neurophysiol*; 1972, 32, pp. 281-294.

Raggenbass, Mario et al.; Nicotinic Receptors in Circuit Excitability and Epilepsy; *J Neurobiol*; Dec. 2002, 53(4) pp. 580-589.

Ragona, Rosario et al.; Management of Parotid Sialocele With Botulinum Toxin; *Laryngoscope*; Aug. 1999, 109(8), pp. 1344-1346.

Rand, Robert W. et al.; Intratumoral Administration of Recombinant Circularly Permuted interleukin-4-Pseudomonas Exotoxin in Patients with High-Grade Glioma; *Clinical Cancer Research*; 6(6), 2157, pp. 1-16 Abstract, Jun. 2000.

Rico, Beatriz et al.; A population of cholinergic neurons is present in the macaque monkey thalamus; *European Journal of Neuroscience*; vol. 10, 1998, pp. 2346-2352.

Rogawski, Michael et al.; Antiepileptic Drugs: Pharmacological Mechanisms and Clinical Efficacy with Consideration of Promising Developmental Stage Compounds; *Pharmacological Reviews*; vol. 42, No. 3, pp. 223-286, 1990.

Sanchez-Prieto, Jose et al.; Botulinum toxin A blocks glutamate exocytosis from guinea-pig cerebral cortical synaptosomes; *Eur. J. Biochem*; 165, 1987; pp. 675-681.

Schafer, M.K. et al.; Cholinergic Neurons and Terminal Fields Revealed by Immunohistochemistry for the Vesicular Acetycholine Transporter. I. Central Nervous System; *Neuroscience*; vol. 84, No. 2, 1998, pp. 331-359.

Schantz, Edward J. et al.; Preparation and Characterization of Botulinum Toxin Type A for Human Treatment; Therapy with Botulinum Toxin; edited by Jankovic et al.; published by Marcel Dekker, Inc., Chp 3, pp. 41-49, 1994.

Scharfen, Cindy et al.; High A*ctivity Iodine-125 Interstitial Implant for Gliomas*; Int J Radiation Oncology Biol Phys; vol. 24, pp. 583-591, 1992.

Schuurman, P. R. et al.; A Comparison of Continuous Thalamic Stimulation and Thalamotomy for Suppression of Severe Tremor; *The New England Journal of Medicine*; Feb. 17, 2000, vol. 342, No. 7, pp. 461-468.

Singh, Bal Ram; Critical Aspects of Bacterial Protein Toxins; *Natural Toxins II*, edited by Singh et al., Plenum Press, New York, 1996, Chp 4, pp. 63-84.

Sloop, Richard r. et al.; Reconstituted botulinum toxin type A does not lose potency in humans if it is refrozen or refrigerated for 2 weeks before use; *Neurology*; 48, Jan. 1997, pp. 249-253.

Speelman, J.D. et al.; Thalamic Surgery and Tremor; *Movement Disorders*; vol. 13, Suppl 3, 1998, pp. 103-106.
Steriade, M. et al.; editors, *Brain Cholinergic Systems*; Oxford University Press, 1990, pp. 136.
Steriade, M. et al.; Parallel activation of thalamic and cortical neurons by brainstem and basal forebrain cholinergic systems; *Brain Cholinergic Systems*; Oxford University Press, 1990, Chp 1, pp. 4-64.
Stone, Trevor W., editor, *CNS Neurotransmitters and Neuromodulators Acetylcholine*; CRC Press, 1995, pp. 16.
Sun, Bomin et al.; Reduction of Hippocampal-Kindled Seizure Activity in Rats by Stereotactic Radiosurgery; *Experimental Neurology*; 154, 1998, pp. 691-695.
Sutula, Thomas P.; Sprouting as an underlying cause of hyperexcitability in experimental models and in the human epileptic temporal lobe; *Epilepsy: Models, Mechanisms, and Concepts*; edited by Schwartzkroin, Cambridge Univ Press, Chp 9, pp. 304-322, 1993.
Talairach, Jean et al.; editors, *Co-Planar Stereotaxic Atlas of the Human Brain*; Chapter 1: Direct and Indirect Radiologic Localization pp. 1-4 and Chapter 2: Reference System: Basal Brain Line CA-CP pp. 5-8, 1988, Thieme Medical Publishers, Inc., N.Y.
Tasker, Ronald R. et al.; Surgical Treatment of the Dystonias; *Textbook of Stereotactic and Functional Neurosurgery*; edited by Gildenberg et al.; Chp 105, pp. 1015-1032, 1997.
Tarsy, D.; Botulinum Toxin Treatment is not Effective for Epilepsy Partialis Continua; *Movement Disorders*; 1995, 10(3) pp. 357-358.
Tracey, David J. et al; editors *Neurotransmitters in the Human Brain*; Plenum Press, 1995, pp. 136-139.
Trudeau, Louis-Eric et al.; Modulation of an early step in the secretory machinery in hippocampal nerve terminals; *Neurobiology*; vol. 95, Issue 12, Jun. 9, 1998, pp. 7163-7168, Abstract.
Wang, Lu-Yang et al.; High-frequency firing helps replenish the readily releasable pool of synaptic vesicles; *Nature*; vol. 394, Jul. 23, 1998, pp. 384-388.
Wiebe, Samuel et al.; A Randomized, controlled Trial of Surgery for Temporal-Lobe Epilepsy; The New England Journal of Medicine; vol. 345, No. 5, Aug. 2, 2001, pp. 311-318.
Wiegand, H. et al.; I-Labelled Botulinum A Neurotoxin: Pharmacokinetics in Cats after Intramuscular Injection; *Naunyn-Schmiedeberg's Arch Pharmacol*; 292, 1976, pp. 161-165.

* cited by examiner

INTRACRANIAL BOTULINUM TOXIN THERAPY FOR FOCAL EPILEPSY

CROSS REFERENCE

This application is a continuation in part of Ser. No. 09/903,849, filed Jul. 12, 2001 now abandoned, which is a divisional of Ser. No. 09/596,306, filed Jun. 14, 2000, now U.S. Pat. No. 6,306,403, which prior patent application and patent are incorporated herein by reference in their entireties.

BACKGROUND

The present invention relates to methods for treating movement disorders. In particular, the present invention relates to methods for treating epilepsy by intracranial administration of a botulinum toxin.

Intracranial Drug Delivery

A major impediment to therapeutic treatment of a neurodegenerative disease, such as various movement disorders, is the blood-brain barrier which significantly limits penetration of the brain by even small molecules from the bloodstream upon peripheral administration of a pharmaceutical. To circumvent the blood-brain barrier direct infusion of various bioactive substances has been carried out. Most clinical experience is with intraventricular (i.e. into a cerebral-spinal fluid [CSF] filled ventricle of the brain) drug delivery. Thus, ventricular infections have been treated by direct infusion of antibiotic. Additionally, intraventricular infusion: of baclofen to treat spasticity; various chemotherapeutics, radiolabelled antibodies, and cytokines to treat brain tumors; cholinergic agonists and Nerve Growth Factor (NGF) to treat Alzheimer's disease, and; dopamine to treat Parkinson's disease is known. Unfortunately, there is a brain-CSF barrier such that penetration of drugs into brain tissue from CSF is suboptimal. Intraventricular drug delivery has therefore been met with limited success in the treatment of, for example, solid tumors, neurodegenerative diseases (such as movement disorders) and other intraparenchymal pathology.

The drawbacks and deficiencies of intraventricular drug delivery has led to increasing interest in direct infusion of drugs into brain parenchyma. Administration of therapeutic bioactive substances to various brain sites of interest has be achieved with reproducible submillimeter precision using modern stereotactic techniques. Thus, intraparenchymal infusion of lidocaine, muscimol and NGF have been used to treat Parkinson's disease, and intraparenchymal infusion of KCL has been used to treat epilepsy. The most widespread use of direct intracerebral clinical administration of a bioactive substance has been to treat brain tumors, which has included gene therapy by delivery of one or more therapeutic genes into brain tumor cells. See e.g. Kaplitt M. G. et al., *Surgical drug delivery for neurodegenerative diseases*. Clin Neurosurg 48; 127-144: 2001. The localized microinjection of lidocaine and muscimol has been found to selectively inactivate focal neuronal activity in the subthalamic nucleus of Parkinson's disease patients (Levy R. et al., *Lidocaine and muscimol microinjections in subthalamic nucleus reverse Parkinsonian symptoms*, Brain 2001 October; 124 (Pt 10):2105-18). The effect is transient and is directly attributable to intrinsic activity and pharmacological half-lives of these agents.

Additionally, patients with malignant gliomas have been treated with a chimeric toxin composed of the cytokine, IL-4, and *Pseudomonas* exotoxin, administered through stereotactic catheter implantation into tumors through small-twist drill holes. Despite varying volumes of infusion, no profound neural or systemic toxicity resulted. Rand R. W. et al., *Intratumoral administration of recombinant circularly permuted interleukin-4-Pseudomonas exotoxin in patients with high-grade glioma*, Clin Cancer Res 6; 2157-2165: 2000.

Thus, precise intracranial therapeutic delivery of bioactive macromolecules can be achieved through stereotactic methodologies. When a molecule is introduced into the extracellular space in brain tissue, because of the narrowness and irregularity of channels, it diffuses through the tissue at a rate which is at least twelve times slower than diffusion of the molecule through agar. Penn R., *The future of CNS infusion systems*, chapter 218, pages 2073-2076 of Gildenberg, P., *Textbook of Stereotactic and Functional Neurosurgery*, McGraw-Hill (1998). Due to take up by cells, binding of receptors or extracellular matrix, enzymatic degradation, or elimination by the vascular system it is unusual for a bioactive molecule applied as a point source to diffuse in brain tissue more than a few millimeters from its' site of administration. Ibid. For functional stereotactic surgeons the type of applications most suited for intraparenchymal drug application are those in which a small lesion or local electrical stimulation has already proved effective, such as for the treatment of tremor. Thus, it has been postulated that the use of selective neurotransmitter agents or antagonists may be more effective to inhibit specific neurons than is current therapies of deliberately making or inducing a lesion (i.e. by radiation, thermal, cryo or electrical ablation or surgical incision) that indiscriminately destroys neurons and axons. Ibid.

Movement Disorders

A movement disorder is a neurological disturbance that involves one or more muscles or muscle groups. Movement disorders include Parkinson's disease, Huntington's Chorea, progressive supranuclear palsy, Wilson's disease, Tourette's syndrome, epilepsy, and various chronic tremors, including essential tremor, tics and dystonias. Different clinically observed movement disorders can be traced to the same or similar areas of the brain. For example, abnormalities of basal ganglia (a large cluster of cells deep in the hemispheres of the brain) are postulated as a causative factor in diverse movement disorders.

Tremors are characterized by abnormal, involuntary movements. An essential tremor is maximal when the body part afflicted (often an arm or hand) is being used, for example when attempts at writing or fine coordinated hand movements are made. Typical chemotherapy is use of the drug propranolol (Inderal) which has the side effects of low blood pressure and heart rate changes. A resting tremor is common in Parkinson's disease and in syndromes with Parkinsonian features. A resting tremor is maximal when the extremities are at rest. Often, when a patient attempts fine movement, such as reaching for a cup, the tremor subsides. Systemic anticholinergic medications have been used with some success.

Dystonias are involuntary movement disorders characterized by continued muscular contractions which can result in twisted contorted postures involving the body or limbs. Causes of dystonia include biochemical abnormalities, degenerative disorders, psychiatric dysfunction, toxins, drugs and central trauma. Thalamotomy and/or subthalamotomy or campotomy are currently the preferred neurosurgical procedures to treat dystonia, and are carried out with techniques and brain targets similar to the surgical treatment of Parkinson's disease. Tasker R., *Surgical Treatment of the*

Dystonias, chapter 105, pages 1015-1032, in Gildenberg P. L. et al., *Textbook of Stereotactic and Functional Neurosurgery*, McGraw-Hill (1998).

Particular dystonias can include spasmodic torticolis, blepharospasm and writer's cramp. Spasmodic torticollis is a syndrome that usually affects adults, and involves the involuntary turning of the neck to one side. Some individuals may not even notice initially that the head and neck are turned. Blepharospasm is an involuntary movement which involves intermittent forceful closure of the eyelids. Writer's cramp is a cramping abnormal posture which develops when one is writing, or performing other actions with the hands. Symptoms may progress to involve the arm and shoulder.

Tic disorders (including Tourette's) are usually very rapid, short lived stereotyped repeated movements. The more common tics involve the motor systems, or are vocal in nature. Motor tics often involve the eyelids, eyebrows or other facial muscles, as well as the upper limbs. Vocal tics may involve grunting, throat clearing, coughing or cursing. Individuals with tic disorders will often describe a strong urge to perform the particular tic, and may actually feel a strong sense of pressure building up inside of them if the action is not performed. For example, a motor tic that may involve the abrupt movement of one of the arms may be controllable for a short period of time if the affected person sits on his hands; however, the almost irresistible urge to do the action often takes over and result in the tic action.

Tourette's syndrome is a tic disorder which often begins in childhood or adolescence and is much more common in males. There are both multiple motor tics, as well as vocal tics present. The tics often change from involvement of one body part to another, and the disease often gets better and worse intermittently, with periods of almost minimal activity, and other times when some patients have difficulty functioning. Other neurobehavioral difficulties often accompany the syndrome. These include attention deficit hyperactivity disorder (ADHD) and obsessive-compulsive disorder. Treatment of most tic disorders employs the use of medications that decrease the amount of dopamine in the brain, such as dopamine antagonists. Unfortunately these drugs are associated with side effects such as other movement disorders, including Parkinsonism (stiffness, slow movement and tremors). In addition to Tourette's syndrome, tics may be associated with head injury, carbon monoxide poisoning, stroke, drug use and mental retardation.

Progressive supranuclear palsy is a movement disorder in which patients have significant difficulty moving their eyes vertically (up and down) initially, followed by all eye movements become limited (ophthalmoplegia). Patients can also develop dementia, rigidity, bradykinesia (slow movements) and a propensity for falls.

Huntington's chorea is a genetically inherited disorder that has both neurological and psychiatric features. Most cases develop when people are in their forties or fifties, but early and late onset is also possible. The disease may begin with either the neurological or mental status changes. The neurological symptoms may vary, but include chorea. Chorea (derived from a Greek word meaning, "to dance") is a series of movements that is dance-like, jerky, brief, and moves from one part of the body to another. Clumsiness, fidgetiness and jumpiness may also occur. Facial movements, especially around the jaw, may occur. There is often difficulty with walking and posture. The psychiatric symptoms may present as paranoia, confusion, or personality changes. As the disease progresses, a significant dementia develops. MRI brain imaging may show atrophy (shrinkage) of a portion of the basal ganglia (involved in movement) that is known as the caudate nucleus.

Wilson's disease is a disorder that involves the nervous system and liver function. The neurological problems include tremors, incoordination, falling, slurred speech, stiffness and seizures. Psychiatric problems can occur and patients can develop severe liver damage if this affliction is untreated. Elevated copper and ceruloplasmin levels are diagnostic.

Unfortunately, a movement disorder, including those set forth above, can become resistant to drug therapy. Drug resistant tremors can include resting tremors, such as can occur in Parkinson's disease, and action tremors, such as essential tremor, multiple sclerosis tremors, post traumatic tremors, post hemiplegic tremors (post stroke spasticity), tremors associated with neuropathy, writing tremors and epilepsy.

Parkinson's Disease

Parkinson's disease is a movement disorder of increasing occurrence in aging populations. Parkinson's disease is a common disabling disease of old age affecting about one percent of the population over the age of 60 in the United States. The incidence of Parkinson's disease increases with age and the cumulative lifetime risk of an individual developing the disease is about 1 in 40. Symptoms include pronounced tremor of the extremities, bradykinesia, rigidity and postural change. A perceived pathophysiological cause of Parkinson's disease is progressive destruction of dopamine producing cells in the basal ganglia which comprise the pars compartum of the substantia nigra, a basal nuclei located in the brain stem. Loss of dopamineric neurons results in a relative excess of acetylcholine. Jellinger, K. A., *Post Mortem Studies in Parkinson's Disease—Is It Possible to Detect Brain Areas For Specific Symptoms?*, J Neural Transm 56 (Supp); 1-29:1999.

Parkinson's disease is a progressive disorder which can begin with mild limb stiffness and infrequent tremors and progress over a period of ten or more years to frequent tremors and memory impairment, to uncontrollable tremors and dementia.

Drugs used to treat Parkinson's disease include L-dopa, selegiline, apomorphine and anticholinergics. L-dopa (levo-dihydroxy-phenylalanine) (sinemet) is a dopamine precursor which can cross the blood-brain barrier and be converted to dopamine in the brain. Unfortunately, L-dopa has a short half life in the body and it is typical after long use (i.e. after about 4-5 years) for the effect of L-dopa to become sporadic and unpredictable, resulting in fluctuations in motor function, dyskinesias and psychiatric side effects. Additionally, L-dopa can cause B vitamin deficiencies to arise.

Selegiline (Deprenyl, Eldepryl) has been used as an alternative to L-dopa, and acts by reducing the breakdown of dopamine in the brain. Unfortunately, Selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects.

Systemically administered anticholinergic drugs (such as benzhexol and orphenedrine) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth and urine retention. See e.g. Playfer, J. R., *Parkinson's Disease*, Postgrad Med J, 73; 257-264:1997 and Nadeau, S. E., *Parkinson's Disease*, J Am Ger Soc, 45; 233-240:1997.

Before the introduction of L-dopa in 1969, stereotactic surgery offered one of the few effective treatments for Parkinson's disease. The significant known deficiencies and drawbacks associated with therapeutic drugs to treat Parkinson's disease, including the long term limitations of L-dopa therapy have led to renewed interest in neurosurgical intervention. Unilateral stereotactic thalamotomy has proven to be effective for controlling contralateral tremor and rigidity, but carries a risk of hemiparesis. Bilateral thalamotomy carries an increased risk of speech and swallowing disorders resulting. Stereotactic pallidotomy, surgical ablation of part of the globus pallidus (a basal ganglia), has also be used with some success. Aside from surgical resection, high frequency stimulating electrodes placed in the ventral intermedialis nucleus has been found to suppress abnormal movements in some cases. A variety of techniques exist to permit precise location of a probe, including computed tomography and magnetic resonance imaging. Unfortunately, the akinesia, speech and gait disorder symptoms of Parkinson's disease are little helped by these surgical procedures, all of which result in destructive brain lesions.

Epilepsy

Epilepsy is the most common serious neurological disorder (Shorvon, S., *Epidemiology, classification, natural history, and genetics of epilepsy*, Lancet 1990 Jul. 14; 336 (8707):93-6; McNamara J., *The neurobiological basis of epilepsy*, Trends Neurosci 1992 October; 15(10):357-9. A seizure is a neurological dysfunction which results from abnormal, excessive, hypersynchronous discharges from an aggregate of central nervous system neurons. A seizure can be manifested behaviorally (if motor systems are involved) or electrographically. Epilepsy describes a condition in which a person has recurrent seizures due to a chronic, underlying process. Although there are various epilepsy syndromes in which the clinical and pathologic characteristics differ the common underlying etiology is neuronal hyperexcitability. Thus, epilepsy encompasses disorders of central nervous system (CNS) hyperexcitability, characterized by chronic, recurrent, paroxysmal changes in neurological function that can be categorized according to electroencephalographic and clinical presentation (Dichter M., *Basic mechanisms of epilepsy: targets for therapeutic intervention*, Epilepsia 1997; 38 Suppl 9:S2-6).

Excluding neonatal febrile seizures, the estimated occurrence of epilepsy in the general population is about 0.5%-1% (Barnes D., *Debate about epilepsy: what initiates seizures?*, Science 1986 Nov. 21; 234(4779):938-40, erratum in Science 1987 Jan. 2; 235(4784):16; Rogawski M., et al., *Antiepileptic drugs: pharmacological mechanisms and clinical efficacy with consideration of promising developmental stage compounds*, Pharmacol Rev 1990 September; 42(3):223-86). Severe, penetrating head trauma is associated with up to a 50% risk of leading to epilepsy. Other causes of epilepsy include stroke, infection and genetic susceptibility.

While recurrent seizures are a hallmark of epilepsy, isolated, nonrecurrent seizures can occur in otherwise healthy individuals for a variety of reasons, such as poisoning, and such individuals are not considered to have epilepsy (Dichter 1997, Ibid). Epileptic seizures are broadly categorized into two groups: focal (partial) and generalized seizures. Focal seizures arise from abnormal activity of a limited group of neurons in cortical or subcortical regions of the brain. The underlying structural abnormality or lesion can develop as a result of birth injury, head trauma, tumor, abscess, infarction, vascular malformation or genetic disease (Dichter 1997, Ibid). The location of the focal activity can be identified by the clinical seizure presentation or may be cryptic. Equivalently, the active focus may not involve the lesion itself but may arise in adjacent or distant (but connected) neuronal populations, supporting the hypothesis of plastic synaptic reorganization underlying focal hyperexcitability. See e.g. Prince D. A., *Epileptogenic neurons and circuits*. In: *Jasper's Basic Mechanisms of the Epilepsies*, Third Edition (1999), Delgado-Escueta A. V., et al., editors), Advances in Neurology 79: 665-684.

Focal seizures are termed "simple" if there is no apparent change in consciousness, otherwise they are termed "complex". Complex focal seizures involve the temporal lobe and limbic system, and are the most common manifestation of epilepsy in adults. Focal seizures that spread to become bilateral electrographically, with concomitant loss of consciousness and with or without motor manifestations, are said to be secondarily generalized. Primary generalized seizures initiate with bilateral electrographic activity, loss of consciousness, and with or without motor convulsions. Focal epilepsy can involve almost any part of the brain and usually results from a localized lesion of functional abnormality. One type of focal epilepsy is the psychomotor seizure. Current therapy for focal epilepsy includes use of an EEG to localize abnormal spiking waves originating in areas of organic brain disease that predispose to focal epileptic attacks, followed by surgical excision of the focus to prevent future attacks.

While the etiology of epilepsy can be multiple, the pathophysiology of epilepsy (in terms of the generation of synchronized neuronal activity) is thought to consistently reflect both fundamental changes in basic neuronal physiological properties together with enhanced synaptic plasticity. The process of epileptogenesis therefore involves a limited range of intrinsic cellular changes that lead to neuronal imbalances in net excitation or inhibition, or in the enhanced excitatory coupling of neuronal aggregates (Prince 1999 ibid, and; Prince D. A., *Cellular mechanisms of interictal-ictal transitions*. In: *Mechanisms of Epileptogenesis. The Transition to Seizure*, Dichter M. A., editor, Plenum Press, New York, 57-71 (1998)). The hallmark of epileptogenesis is the appearance of interictal (between seizure) bursts or discharges. This pattern of activity is observed on the EEG record as brief (80-200 millisecond), large, sharp spikes against an otherwise normal background of activity (McCormick and Contreras 2001, supra). These periodic EEG spikes correlate to prolonged cellular depolarizations (paroxysmal depolarization shift, PDS), while the quiescent periods reflect phases of cellular hyperpolarization.

Thus it is believed that distinct neural circuitry underlying the initiation and propagation of seizures can be identified for each type of epileptic seizures because seizures are manifestations of abnormal activity in neuronal networks that normally are engaged in routine physiological processes (Gale K., *Focal trigger zones and pathways of propagation in seizure generation*. In: *Epilepsy: Models, Mechanism and Concepts*, Schwartzkroin P. A., editor, Cambridge University Press, U.K., pages 48-93 (1993)).

While there may be no dedicated "seizure circuit" within the brain, seizure propagation clearly results from, and depends upon, the specific neuroanatomy of the interconnected neuronal circuitry. It is well established that some parts of the brain, such as the limbic system, are more susceptible to epileptogenesis and seizure propagation than are other areas, such as the neocortex. The hippocampus (a part of the limbic system) has been extensively studied, as much for its orderly and accessible cellular architecture as for its tendency to be become epileptogenic when provided an appropriate stimulus, both in vitro and in vivo. The epileptogenic hippocampus displays significant synaptic reorganization and changes in plasticity that potentiate hyperexcitability.

Mossy fiber sprouting, secondary to loss of target cells in Ammon's horn area CA3 of the hippocampus, and subsequent establishment of synapses in the inner molecular layer of the normally hypoexcitable dentate gyrus (fascia dentata), results in recurrent (feedback) excitation (Sutula T. P., *Sprouting as an underlying cause of hyperexcitability in experimental models and in the human epileptic temporal lobe*. In: *Epilepsy: Models, Mechanism and Concepts*, Schwartzkroin P. A. editor, Cambridge University Press, U.K., pages 304-322 (1993)). This synchronized hippocampal activity directly results from phasic imbalances between excitatory and inhibitory neuronal populations. The hippocampus, together with the amygdala, have been implicated in human temporal lobe epilepsy, an often intractable condition and the most common epileptic disorder in adults. Cellular degeneration in the hippocampus (termed hippocampal sclerosis), and compensatory changes in wiring, are a prime cause of hyperexcitability and a rationale for resective surgery in the treatment of temporal lobe epilepsy. As previously noted, the neocortex is less vulnerable to seizure propagation from local foci as compared to the limbic system. This self-limiting capacity may arise from the inherent characteristic of selective presynaptic depression of excitatory transmission under conditions of high frequency firing (Galaretta M. et al., *Frequency-dependent synaptic depression and the balance of excitation and inhibition in the neocortex*, Nature Neurosci 1(7); 587-594: 1998), as would occur during seizure propagation. Changes in the connectivity and communication between neuronal cells (neural plasticity) have been implicated in the pathophysiology of epilepsy. Synaptic plasticity refers to characteristic activity-dependent changes in synaptic efficacy that may either produce enhancement (long term potentiation, LTP) or inhibition (long term depression). The observed changes may reflect altered functionality at presynaptic and postsynaptic locations. Presynaptic changes, which involve alterations in the kinetics of synaptic vesicle recycling, affect the rate of neurotransmission and, therefore, of synaptic activity (Staley K., et al., *Presynaptic modulation of CA3 network activity*, Nat Neurosci 1998 July; 1(3):201-9, erratum in Nat Neurosci 1998 August; 1(4):331; Wang L., et al., *High-frequency firing helps replenish the readily releasable pool of synaptic vesicles*, Nature 1998 Jul. 23; 394(6691):384-8; Zakharenko S., et al., *Visualization of changes in presynaptic function during long-term synaptic plasticity*, Nat Neurosci 2001 July; 4(7):711-7). Synchronization of presynaptic and postsynaptic activity can also enhance the efficacy of synaptic transmission and facilitate LTP (Ganguly K., et al., *Enhancement of presynaptic neuronal excitability by correlated presynaptic and postsynaptic spiking*, Nat Neurosci 2000 October; 3(10):1018-26). Postsynaptic changes in synaptic plasticity have been suggested as the basis for such processes as learning and memory and may contribute, in part, to the process of epileptogenesis.

This neuroanatomical basis for brain neuronal network connectivity, and the mechanisms of epileptogenesis have been investigated, for example, in the kindling model of focal, temporal lobe (limbic) epilepsy. In the kindling paradigm, test animals are subjected to repeated, focal electrical stimulation through bipolar, stereotactically-implanted depth electrodes (Goddard G. V. et al, *A permanent change in brain function resulting from daily electrical stimulation*. Exp Neurol 25(3); 295-330:1969). The electrodes are typically placed in either the amygdala or dorsal hippocampus of rats. The initially subconvulsive stimulations gradually precipitate a described progression of behavioral manifestations, which are then scored (Racine R. J., *Modification of seizure activity by electrical stimulation. II. Motor seizure*, Electroencephalogr Clin Neurophysiol. 32(3); 281+-94: 1972b), and which correlate to the gradual electrographic appearance of afterdischarges (episodic, ictal, electrical activity in the absence of exogenous stimulus). Together with their appearance, the threshold electrical stimulus required to produce an afterdischarge gradually lowers, paralleling the seizure threshold drop seen in human epileptogenesis. The kindling process fails to develop in the absence of afterdischarges (Racine R. J., *Modification of seizure activity by electrical stimulation. I. After-discharge threshold*, Electroencephalogr Clin Neurophysiol. 32(3); 269-79:1972a). Eventually, the continued repeated stimulations precipitate full motor seizures (Goddard et al, 1969, supra). Once established, the lowered seizure threshold and hyperexcitability are permanent, such that an otherwise subconvulsive (threshold) stimulus at a later time point triggers a generalized, convulsive seizure. It should be noted that the generalized seizure is simply an end point, reflecting recruitment of motor output pathways, and does not in and of itself establish the kindled phenotype. Rather, kindling reflects the whole process of population recruitment and spread by repeated focal afterdischarge.

Antiepileptic drug ("AED") therapy is the mainstay of treatment for most patients with epilepsy and a variety of drugs have been used. See e.g., Fauci, A. S. et al., *Harrison's Principles of Internal Medicine*, McGraw-Hill, 14$^{th}$ Edition (1998), page 2321. About twenty percent of patients with epilepsy are resistant to drug therapy despite efforts to find an effective combination of antiepileptic drugs. Surgery can then be an option. Thus, patients with refractory epilepsy and intractable seizures can be candidates for surgical resection followed by up AED therapy. Surgery is superior to long-term drug treatment alone in the management of temporal lobe epilepsy (Wiebe et al, 2001, supra). Typically, video-electroencephalogram (EEG) monitoring is used to broadly define the anatomic location of the seizure focus and to correlate the abnormal electrophysiological activity with behavioral manifestations of the seizure. Scalp or scalp-sphenoidal recordings are usually sufficient for localization. Functional imaging studies such as SPECT and PET, as well as direct electrophysiological analysis (subdural or depth electrode mapping) are adjunctive tests that can help verify the localization of an apparent epileptogenic region with an anatomic abnormality. A high resolution MRI scan is routinely used to identify structural lesions. Once the presumed location of the seizure onset is identified, additional studies, including neuropsychological testing and the intracarotid amobarbital test (Wada's test) can be used to assess language and memory localization and to determine the possible functional consequences of surgical removal of the epileptogenic region. In some cases, the exact extent of the resection to be undertaken can be determined by performing cortical mapping at the time of the surgical procedure. This involves electrophysiologic recordings and cortical stimulation of the awake patient to identify the extent of epileptiform disturbances and the function of the cortical regions in questions. Clearly, consideration for surgery is contingent upon the identified and implicated substructure being resectable. The most common surgical procedures for patients with temporal lobe epilepsy are resection of the anteromedial temporal lobe (temporal lobectomy, which includes the nterolateralneocortex and the deeply located older structures—corticoamygdalohippocampectomy), or a more limited removal of the underlying hippocampus and amygdala (selective amygdalohippocampectomy. A third procedure, the selective neocortical resection, is rarely used, although focal seizures arising from extratemporal regions may be suppressed by a focal neocortical resection.

While invasive, surgery has proven to be superior to long-term drug treatment alone in the management of temporal lobe epilepsy (Wiebe S. et al, *A randomized, controlled trial of surgery for temporal-lobe epilepsy*, N Engl J Med 345(5): 311-8:2001). Unfortunately, about 5% of patients can still develop clinically significant complications from surgery and up to 10% of temporal lobectomy patients can still have seizures. Kwan P. et al, *Refractory epilepsy: a progressive, intractable but preventable condition?* Seizure 11: 77-84:2002). In cases where subcortical structures encompass, or are in proximity to, critical functional areas, and thus cannot be approached with standard resective techniques, the treatment regimen can be a maintenance of multiple AEDs for suppression of seizure activity (Kwan et al 2002, supra).

Stereotactic surgical procedures have been refined and aided by improvements in current imaging techniques, permitting precise identification and targeting of intracranial substructures, compared to more traditional ventriculography. MRI methods allow for clear and accurate definition, three-dimensional spatial orientation and structure localization. See e.g. Landi A. et al., *Accuracy of stereotactic localization with magnetic resonance compared to CT scan: experimental findings*, Acta Neurochir (Wien) 143; 593-601: 2001. As compared to historically traditional craniotomy and resective surgery, stereotactic surgery (as with, for example, refractive temporal lobe epilepsy) may be better tolerated by patients and more economical to perform. Parrent A. G. et al., *Stereotactic surgery for temporal lobe epilepsy*, Can J Neurol Sci 27(Suppl 1); S79-S84: 2000. In addition to guiding surgical resections, stereotactic techniques can be employed, alternatively, to specifically target a selected structure and deliver an effective therapy. While all surgical procedures are invasive and irreversible, stereotactically targeted therapies may be either invasive or noninvasive, and either irreversible or reversible.

Stereotactic radiofrequency ablation (invasive, irreversible) has been described for the treatment of intractable gelastic seizures arising from a hypothalamic hamartoma following MR imaging, focus localization and reference-based guidance of the lesioning electrode to the hypothalamus. See e.g. Parrent A. G., *Stereotactic radiofrequency ablation for the treatment of gelastic seizures associated with hypothalamic hamartoma: case report*, J Neurosurg 91: 881-884: 1999. Similarly, and in a manner analogous to that applied to the treatment of Parkinson's disease, stereotactic stimulation at high radiofrequency (130 Hz) of the subthalamic nucleus (STN, corpus luysi) has shown efficacy in seizure control in the absence of apparent anatomical lesioning. In the latter case, the STN was not the focus per se and the stimulation protocol affected the network propagation of seizures rather than the source focus itself. Benabid A. L. et al., *Deep brain stimulation of the corpus luysi (subthalamic nucleus) and other targets in Parkinson's disease. Extension to new indications such as dystonia and epilepsy*, J Neurol 248(Suppl 3); 37-47: 2001.

Stereotactic radiosurgery (radiotherapy) is a noninvasive but irreversible procedure involving guided, selective irradiation of a targeted substructure, and has been described for the treatment of seizures arising from a temporal focus. Cmelak A. J. et al., *Low-dose stereotactic radiosurgery is inadequate for medically intractable mesial temporal lobe epilepsy: a case report*, Seizure 10; 442-446; 2001. Heikkinen E. R. et al., *Stereotactic radiotherapy instead of conventional epilepsy surgery. A case report*, Acta Neurochir (Wien) 119(1-4); 159-160: 1992. The effectiveness of radiotherapy is dose-dependent in both clinical (10 Gy, Heikkinen et al, 1992; 15 Gy, Cmelak et al, 2001) and experimental application (40 Gy, Sun B. et al., *Reduction of hippocampal-kindled seizure activity in rats by stereotactic radiosurgery*, Exper Neurol 154; 691-695: 1998). Lower dose effects are equivocal while higher doses are effective; however, higher doses also produce histological, irreversible changes not seen at lower doses. Thus, anatomical lesioning of the target structure appears to be important in the efficacy of stereotactic radiosurgery, but may introduce dose-dependent toxicity issues.

Stereotactic procedures can also be used to guide the direct delivery of pharmacologically active agents into specific, localized substructures. These agents may result in either permanent (irreversible) lesions, such as with excitotoxins (e.g. kainic and ibotenic acids), or reversible inactivation, such as with anesthetics and neurotransmitter iontophoresis. Lomber S. G., *The advantages and limitations of permanent or reversible deactivation techniques in the assessment of neural function*, J Neurosci Meth 86; 109-117: 1999. Delivery may be achieved through both hypodermic cannulae and fine-tipped micropipettes, or variations thereof. Malpeli J. G., *Reversible inactivation of subcortical sites by drug injection*, J Neurosci Meth 86; 119-128: 1999. Stereotactic placement of electrodes to record intracranial EEG has been described together with simultaneous metabolic assessment through microdialysis sampling of the target. Fried I. et al., *Cerebral microdialysis combined with single-neuron and electroencephalographic recording in neurosurgical patients*, J Neurosurg 91; 697-705: 1999. Thus, it is possible, to configure a system to assess the neuronal activity within the desired target before, during and after delivery of the pharmacological agent. With any such procedure, assessment of the spatial distribution (spread) of the agent within the target structure can also be determined. Malpeli, 1999, supra; Martin J. H. et al., *Pharmacological inactivation in the analysis of the central control of movement*, J Neurosci Meth 86; 145-159: 1999. Apart from neuronal activity measured through indwelling depth electrodes, functional (metabolic) assessments can be made with PET imaging to determine the profile and duration of effects of the active agent on the target in question.

In cases where subcortical structures encompass, or are in proximity to, critical functional areas, and thus cannot be approached with standard resective techniques, the treatment regimen may be a maintenance of multiple AEDs for suppression of seizure activity (Kwan and Brodie, 2002 ibid). For functionally critical (eloquent) cortical regions that cannot be approached with standard resective surgical procedures, multiple subpial transections (MST) can be used to treat refractory seizures (Mulligan L. P. et al, *Multiple subpial transections: the Yale experience*. Epilepsia 42(2): 226-229:2001). *new approach to the surgical treatment of focal epilepsy*, J Neurosurg 70: 231-239:1989) This procedure exploits the natural orthogonal architecture of the cerebral cortex, which is arranged such that functional units are organized vertically while intracortical interconnections are primarily horizontal (perpendicular) to the functional barrels. Synchronous epileptic activity can arise through horizontal intracortical spread. The MST procedure physically disrupts these horizontal interconnections while sparing the vertically-oriented cortical function (Morrell F. et al, *Multiple subpial transection: a* The MST procedure physically disrupts these horizontal interconnections while sparing the vertically-oriented cortical function (Morrell et al, 1989 ibid). Thus, MST is a surgical technique for intractable epilepsy which reduces the occurrence of electrocorticographical spikes recorded from the cortical surface and can thereby reduce clinical epileptic events. Significantly, MST permits treatment of unresectable epileptogenic foci, such as foci in functionally important ("eloquent") areas of the cerebral cortex. Resection of eloquent foci can leave an epilepsy patient with a significant reduction in neurological function.

MST has as its' basis the diminution of the spread of electrical activity between nearby superficial cortical neurons and is based upon the anatomic and functional structure of the columnar organization of the higher mammalian neocortex. When used to effectively accomplish a seizure ocus resection, MST reduces the side to side spread of epileptogenic energy along cortical neurons without causing major functional impairment of the centrifugal and centripetal cortical neuronal connections. Thus, MST reduces the horizontal "cross talk" of epileptic discharges in order to prevent the discharge spreading along the cortical service and the resulting seizure.

Brain Motor Systems

Several areas of the cerebrum influence motor activity. Thus, lesion to the motor cortex of the cerebrum, as can result from stoke, can remove inhibition of vestibular and reticular brain stem nuclei, which then become spontaneously active and cause spasm of muscles influenced by, the now disinhibited, lower brain areas.

An accessory motor system of the cerebrum is the basal ganglia. The basal ganglia receives most input from and sends most of its signals back to the cortex. The basal ganglia include the caudate nucleus, putamen, globus pallidus, substantia nigra (which includes the pars compacta) and subthalamic nucleus. Because abnormal signals from the basal ganglia to the motor cortex cause most of the abnormalities in Parkinson's disease, attempts have been made to treat Parkinson's disease by blocking these signals. Thus lesions have been made in the ventrolateral and ventroanterior nuclei of the thalamus to block the feedback circuit from the basal ganglia to the cortex. Additionally, pallidotomy, the surgical ablation of part of the globus pallidus, has been used to effectively treat the motor disorders of Parkinson's disease.

Surgical intervention is believed to assist by interrupting a motoric pathway which, due to a dopaminergic deficiency, had pathologically inhibited the thalamus. The inhibited thalamus in turn understimulates cortical neuronal networks responsible for generating movement. Hence, surgery removes the thalamic inhibition and has been used in the treatment of pharmacoresistant movement disorders. Speelman, J. D., et al., *Thalamic Surgery and Tremor*, Mov Dis 13(3); 103-106:1998.

Intracranial lesions for the treatment of tremor and other parkinsonian symptoms have been made to the globus pallidus and the ansa lenticularis. Long term results of pallidotomy have sometimes been disappointing. Positive results for the surgical arrest of tremor have been obtained by lesioning the following thalamic nuclei: (1) the ventrointermedius (Vim) or ventral lateral posterior (VLp) nucleus; (2) ventrooralis anterior (Voa) nucleus (Voa and Vop have been collectively termed the ventral lateral anterior nucleus (VLa)); (3) ventrooralis posterior (Vop) nucleus; (4) subthalamic nuclei (campotomy), and; (5) CM-Pf thalamic nuclei. Generally, the ventrolateral thalamus has been the surgical target of choice in the treatment of Parkinson's disease and other systemically administered, drug resistant tremors. Brophy, B. P., et al., *Thalamotomy for Parkinsonian Tremor*, Stereotact Funct Neurosurg, 69; 1-4:1997. Thalamic excitation of the cortex is necessary for almost all cortical activity.

Stereotactic surgery (assisted by neuroimaging and electrophysiologic recordings) has been used in the management of advanced, pharmacoresistant Parkinson's disease, targeting hyperactive globus pallidus and subthalamic nuclei. An electrode or a probe is placed into the brain using a brain atlas for reference with assistance from brain imaging by computer tomography or magnetic resonance imaging. Lesions in different parts of the pallidum (i.e. posteroventral pallidum), basal ganglia, thalamus and subthalamic nuclei have been carried out to treat motor disorders of Parkinson's disease. Unfortunately, surgical brain lesions create a risk of impairment to speech, visual and cognitive brain areas. Neurotransplantation shows promise but requires further investigation. Additionally, deep brain stimulation using electrodes for the suppression of tremor using can create problems due to wire erosion, lead friction, infection of the implantable pulse generator, malfunction of the implantable pulse generator, electrical shock and lead migration. Other complications due to electrode stimulation can include dysarthria, disequilibrium, paresis and gait disorder. See e.g. Koller, W. C. et al., *Surgical Treatment of Parkinson's Disease*, J Neurol Sci 167; 1-10:1999, and Schuurman P. R., et al., *A Comparison of Continuous Thalamic Stimulation and Thalamotomy for Suppression of Severe Tremor*, NEJM 342(7); 461-468:2000.

Aside from surgical ablation or stimulation, external radiotherapy (Gamma Knife Radiosurgery) has also been used to a limited extent for the treatment of drug resistant parkinsonian tremors. Drawbacks with this procedure are that the reduction in tremor is delayed by between one week and eight months after the radiosurgery, and that long term benefits as well as radiation side effects are currently unknown.

As set forth, treatment of parkinsonian tremor and other movement disorders has been carried out by thalamotomy and/or interruption of pallidofugal fibers in the subthalamic region and pallidotomy has also been used. Current concepts of basal ganglia circuitry propose that the loss of striatal dopamine in Parkinson's disease leads to overactivity of the striatal projection to the lateral segment of the globus pallidus. The resulting decrease in lateral pallidal activity results in disinhibition of the subthalamic nucleus, its main projection site. Increased subthalamic activity in turn causes overactivity of the internal segment of the globus pallidus, which projects to the pedunculopontine nucleus (PPN) and the ventrolateral (VL) thalamus. Thus, overactivity in the subthalamic nucleus and internal pallidum produces the parkinsonian symptoms of tremor, bradykinesia and hypokinesia through projections to the PPN and VL thalamus. Lesion in the subthalamic nucleus and the results of pallidotomy, particularly posteroventral pallidotomy, have permitted effective treatment of akinesia in parkinsonian patients.

Botulinum Toxin

The genus *Clostridium* has more than one hundred and twenty seven species, grouped according to their morphology and functions. The anaerobic, gram positive bacterium

*Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a LD50 in mice (i.e. 1 unit). One unit of BOTOX® (a botulinum toxin type A purified neurotoxin complex, which is also referred to as a botulinum toxin type A complex) contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapte r 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® (a botulinum toxin type A complex) equals 1 unit). One unit (U) of botulinum toxin is defined as the LD50 upon intraperitoneal injection into female Swiss Webster mice weighing 18 to 20 grams each.

[1] Available from Allergan, Inc., of Irvine, Calif. under the tradename BOTOX® (a botulinum toxin type A complex) in 100 unit vials.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Gonelle-Gispert, C., et al., *SNAP-25a and -25b isoforms are both expressed in insulin-secreting cells and can function in insulin secretion*, Biochem J. 1; 339 (pt 1):159-65:1999, and Boyd R. S. et al., *The effect of botulinum neurotoxin-B on insulin release from a ∃-cell line*, and Boyd R. S. et al., *The insulin secreting ∃-cell line, HIT-15, contains SNAP-25 which is a target for botulinum neurotoxin-A*, both published at *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

The success of botulinum toxin type A to treat a variety of clinical conditions has led to interest in other botulinum toxin serotypes. Additionally, pure botulinum toxin has been used to treat humans. see e.g. Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3):165. Hence, a pharmaceutical composition can be prepared using a pure botulinum toxin.

The type A botulinum toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1987. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [$^3$H]Noradrenaline and [$^3$H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3\times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of 1-2×10$^8$ LD$_{50}$ U/mg or greater; purified botulinum toxin type B with an approximately 156 kD molecular weight with a specific potency of 1-2×10$^8$ LD$_{50}$ U/mg or greater, and; purified botulinum toxin type F with an approximately 155 kD molecular weight with a specific potency of 1-2×10$^7$ LD$_{50}$ U/mg or greater.

Either the pure botulinum toxin (i.e. the 150 kilodalton botulinum toxin molecule) or the toxin complex can be used to prepare a pharmaceutical composition. Both molecule and complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® (a botulinum toxin type A complex) consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® (a botulinum toxin type A complex) can be reconstitued with sterile, non-preserved saline prior to intramuscular injection. Each vial of BOTOX® (a botulinum toxin type A complex) contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX® (a botulinum toxin type A complex), sterile normal saline without a preservative; (0.9% Sodium Chloride Injection) is used by drawing up the proper amount of diluent in the appropriate size syringe. Since BOTOX® (a botulinum toxin type A complex) may be dispersed or denatured by bubbling or similar violent agitation, the diluent is gently injected into the vial. For sterility reasons BOTOX® (a botulinum toxin type A complex) is preferably administered within four hours after the vial is removed from the freezer and reconstituted. During these four hours, reconstituted BOTOX® (a botulinum toxin type A complex) can be stored in a refrigerator at about 2° C. to about 8° C. Reconstituted, refrigerated BOTOX® (a botulinum toxin type A complex) has been reported to retain its potency for at least about two weeks. *Neurology*, 48:249-53:1997.

Botulinum toxins have been used in clinical settings for the treatment of neuromuscular disorders characterized by hyperactive skeletal muscles. Botulinum toxin type A (BOTOX®, a botulinum toxin type A complex) was approved by the U.S. Food and Drug Administration in 1989 for the treatment of essential blepharospasm, strabismus and hemifacial spasm in patients over the age of twelve. In 2000 the FDA approved commercial preparations of type A (BOTOX®, a botulinum toxin type A complex) and type B botulinum toxin MYOBLOC® (a botulinum toxin type B preparation) serotypes for the treatment of cervical dystonia, and in 2002 the FDA approved a type A botulinum toxin (BOTOX®, a botulinum toxin type A complex) for the cosmetic treatment of certain hyperkinetic (glabellar) facial wrinkles. Clinical effects of peripheral intramuscular botulinum toxin type A are usually seen within one week of injection and sometimes within a few hours. The typical duration of symptomatic relief (i.e. flaccid muscle paralysis) from a single intramuscular injection of botulinum toxin type A can be about three months, although in some cases the effects of a botulinum toxin induced denervation of a gland, such as a salivary gland, have been reported to last for several years. For example, it is known that botulinum toxin type A can have an efficacy for up to 12 months (Naumann M, et al., *Botulinum toxin type A in the treatment of focal, axillary and palmar hyperhidrosis and other hyperhidrotic conditions*, European J. Neurology 6 (Supp 4): S111-S115: 1999), and in some circumstances for as long as 27 months. Ragona, R. M, et al., *Management of parotid sialocele with botulinum toxin*, The Laryngoscope 109:1344-1346:1999.

However, the usual duration of an intramuscular injection of Botox® is typically about 3 to 4 months.

It has been reported that botulinum toxin type A has been used in clinical settings as follows:

(1) about 75-125 units of BOTOX® (a botulinum toxin type A complex) per intramuscular injection (multiple muscles) to treat cervical dystonia;

(2) 5-10 units of BOTOX® (a botulinum toxin type A complex) per intramuscular injection to treat glabellar lines (brow furrows) (5 units injected intramuscularly into the procerus muscle and 10 units injected intramuscularly into each corrugator supercilii muscle);

(3) about 30-80 units of BOTOX® (a botulinum toxin type A complex) to treat constipation by intrasphincter injection of the puboreetalis muscle;

(4) about 1-5 units per muscle of intramuscularly injected BOTOX® (a botulinum toxin type A complex) to treat blepharospasm by injecting the lateral pre-tarsal orbicularis oculi muscle of the upper Lid and the lateral pre-tarsal orbicularis oculi of the lower lid.

(5) to treat strabismus, extraocular muscles have been injected intramuscularly with between about 1-5 units of BOTOX® (a botulinum toxin type A complex) the amount injected varying based upon both the size of the muscle to be injected and the extent of muscle paralysis desired (i.e. amount of diopter correction desired).

(6) to treat upper limb spasticity following stroke by intramuscular injections of BOTOX® (a botulinum toxin type A complex) into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachui: 50 U to 200 U. Each of the five indicated muscles has been injected at the same treatment session, so that the patient receives from 90 U to 360 U of upper limb flexor muscle BOTOX® (a botulinum toxin type A complex) by intramuscular injection at each treatment session.

(7) to treat migraine, pericranial injected (injected symmetrically into glabellar, frontalis and temporalis muscles) injection of 25 U of BOTOX® (a botulinum toxin type A complex) has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Lyons, J., et al., *Tremor-Predominant Parkinson's Disease*, Drugs & Aging 16(4); 273-278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January; 71:24-6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as hypersalivation and rhinittis, with a botulinum toxin.

Furthermore, various afflictions, such as hyperhydrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin.

Botulinum toxin has been used to study the release of dopamine from various brain cells, in light of the theory that Parkinson's disease is due to the death of dopamine releasing cell in the striatal region of the brain. See e.g. Bergquist F. et al., *Evidence for different exocytosis pathways in dendritic and terminal dopamine release in vivo*, Brain Research 950; 245-253: (2002), which me determined that in vivo, intracranial microdialysis of a botulinum toxin type A into either the substantia nigra or striatum use of rats strongly reduced release of somatodentritic dopamine from cells therein. Hence, one could conclude that evidence that the death of dopamine releasing cells in either the substantia nigra or substantia striatum regions of the brain can be a factor in the occurrence of Parkinson's disease.

In addition to having pharmacologic actions at the peripheral location, botulinum toxins can also have inhibitory effects in the central nervous system. Work by Weigand et al, ($^{125}$I-labelled botulinum A neurotoxin:pharmacokinetics in cats after intramuscular injection, Nauny-Schmiedeberg's Arch. Pharmacol. 1976; 292,161-165), and Habermann, ($^{125}$I-labelled Neurotoxin from clostridium botulinum A: preparation, binding to synaptosomes and ascent to the spinal cord, Nauny-Schmiedeberg's Arch. Pharmacol. 1974; 281, 47-56) showed that botulinum toxin is able to ascend to the spinal area by retrograde transport. As such, a botulinum toxin injected at a peripheral location, for example intramuscularly, may be retrograde transported to the spinal cord.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

The tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158:1990.

It is known that injection of tetanus toxin into rat cerebral cortex can induce chronic epilepsy and based upon this finding tetanus toxin has been used to provide a model of focal epilepsies. See e.g. Mellanby, J., *Tetanus toxin as a tool for investigating the consequences of excessive neuronal excitation*, pages 291-297 of Dasgupta, B. R., *Botulinum and tetanus neurotoxins*, Plenum Press (1993), and; Jefferys, J. G., et al., *Chronic focal epilepsy induced by intracerebral tetanus toxin*, Ital J Neurol Sci 1995 February-March; 16(1-2):27-32.

Contrary to the result upon intracranial administration of a tetanus toxin, seizures do not result upon intrathecal administration of a botulinum toxin to a mammal (see e.g. U.S. Pat. No. 6,113,915). Additionally, and as set forth above, intoxication with tetanus toxin results in a spastic paralysis, whereas intoxication with a botulinum toxin results in a flaccid paralysis. Intramuscular administration of a botulinum toxin to treat epilepsy has been reported to be ineffective. Tarsy, D. et al., *Botulinum toxin treatment is not effective for epilepsy partialis continua*, Mov Disord 1995; 10(3):357-8.

Additionally, intraventricular injection of tetanus toxin can cause an increase in serotonin levels in rats. Aguilera, J. et al., *Stereotaxic injection of tetanus toxin in rat central nervous system causes alteration in normal levels of monoamines*, J. Neurochem, 56(3); 733-738: 1991.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic, as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Cholinergic Brain Systems

Cholinergic influence of both the motor and visual thalamus originates from both the brainstem and the basal forebrain. See e.g. Billet S., et al., *Cholinergic Projections to the Visual Thalamus and Superior Colliculus*, Brain Res. 847; 121-123:1999 and Oakman, S. A. et al., *Characterization of the Extent of Pontomesencephalic Cholinergic Neurons' projections to the Thalamus: Comparison with Pro-* jections to Midbrain Dopaminergic Groups, Neurosci 94(2); 529-547; 1999. Thus, it is known based on histochemical studies using acetylcholinesterase (AchE) staining and retrograde tracing with choline acetyltransferase (ChAT) immunochemistry that there can be ascending cholinergic stimulation by the brainstem of thalamic neurons. Steriade M. et al., *Brain Cholinergic Systems*, Oxford University Press (1990), chapter 1. Indeed, many thalamic nuclei receive dense cholinergic innervation from brainstem reticular formations. Ibid, page 167. Known brainstem cholinergic cell groups are located within: (1) the rostral pons at what is termed a Ch5 location, which is located within the central tegmental field around the brachium conjunctivum, forming a pedunculopontine tegmental nucleus, and; (2) the caudal part of the midbrain, at what is termed a Ch6 location, the laterodorsal tegmental nucleus, which is embedded in the periaqueductal and periventricular gray matter. The Ch5 and Ch6 cell groups can consist almost exclusively of cholinergic neurons and together form the pontine cholinergic system. The Ch5-Ch6 cholinergic groups provide direct ascending projections that terminate in a number of target structure in the midbrain, diencephalon and telencephalon, including the superior colliculus, anterior pretectal area, interstitial magnocellular nucleus of the posterior commissure, lateral habenular nucleus, thalamus, magnocellular preoptic nucleus, lateral mammillary nucleus, basal forebrain, olfactory bulb, medial prefrontal cortex and pontine nuclei. Stone T. W., *CNS Neurotransmitters and Neuromodulators: Acetylcholine*, CRC Press (1995), page 16. See also Schafer M. K.-H. et al., *Cholinergic Neurons and Terminal Fields Revealed by Immunochemistry for the Vesicular Acetylcholine Transporter. I. Central Nervous System*, Neuroscience, 84(2); 331-359:1998. Three dimensional localization of Ch1-8 cholinergic nuclei have been mapped in humans. See e.g. Tracey, D. J., et al., *Neurotransmitters in the Human Brain*, Plenum Press (1995), pages 136-139.

Additionally, the basal forebrain (proencephalon) provides cholinergic innervation of the dorsal thalamus, as well as to the neocortex, hippocampus, amygdala and olfactory bulb. See e.g. Steridae, page 136-136, supra. Basal forebrain areas where the great proportion of neurons are cholinergic include the medial septal nucleus (Ch1), the vertical branches of the diagonal band nuclei (Ch2), the horizontal branches of the diagonal band nuclei (Ch3), and the magnocellular nucleus basalis (Ch4), which is located dorsolaterally to the Ch3 cell group. Ch1 and Ch2 provide the major component of cholinergic projection to the hippocampus. The cells in the Ch3 sector project to the olfactory bulb.

Furthermore, cholinergic neurons are present in the thalamus. Rico, B. et al., *A Population of Cholinergic Neurons is Present in the Macaque Monkey Thalamus*, Eur J Neurosci, 10; 2346-2352:1998.

Abnormalities in the brain's cholinergic system have been consistently identified in a variety of neuropsychiatric disorders including Alzheimer's disease, Parkinson's disease and dementia with Lewy bodies. Thus, in Alzheimer's disease there is hypoactivity of cholinergic projections to the hippocampus and cortex. In individuals with dementia with Lewy bodies extensive neocortical cholinergic deficits are believed to exist and in Parkinson's disease there is a loss of pedunculopontine cholinergic neurons. Notably, in vivo imaging of cholinergic activity in the human brain has been reported. Perry, et al., *Acetylcholine in Mind: a Neurotransmitter Correlate of Consciousness?*, TINS 22(6); 273-280: 1999

As set forth, current therapies relating to neuronal inhibition, such as resection radiosurgery ablation, microinjection of pharmacological agents confirm that suppression of an epileptogenic focus can arrest seizures. Unfortunately such methods of treating focal epilepsy either provide transient effects, irreversible damage to brain tissue or introduce unwanted toxicity.

What is needed therefore is an intracranial method for effectively treating focal epilepsies by administration of a pharmaceutical which has the characteristics of long duration of activity, low rates of diffusion out of a chosen intracranial target tissue where administered, and nominal systemic effects at therapeutic dose levels.

SUMMARY

The present invention meets this need and provides methods for effectively treating focal epilepsies by intracranial administration of a Clostridial neurotoxin which has the characteristics of long duration of activity, low rates of diffusion out of an intracranial site where administered and insignificant systemic effects at therapeutic dose levels.

The following definitions apply herein:

"About" means approximately or nearly and in the context of a numerical value or range set forth herein means±10% of the numerical value or range recited or claimed.

"Biological activity" includes, with regard to a neurotoxin, the ability to influence synthesis, exocytosis, receptor binding and/or uptake of a neurotransmitter, such as acetylcholine, or of an endocrine or exocrine secretory product, such as insulin or pancreatic juice, respectively.

"Local administration" means direct administration of a pharmaceutical at or to the vicinity of a site on or within a patients' body, at which site a biological effect of the pharmaceutical is desired. Local administration excludes systemic routes of administration, such as intravenous or oral administration.

"Neurotoxin" means a biologically active molecule with a specific affinity for a neuronal cell surface receptor. Neurotoxin includes Clostridial toxins both as pure toxin and as complexed with one to more non-toxin, toxin associated proteins "Intracranial" means within the cranium or at or near the dorsal end of the spinal cord and includes the medulla, brain stem, pons, cerebellum and cerebrum.

"Intraparenchymal" means within the parenchyma of the brain, that is within the tissue (including within an extracellular space of brain tissue) of the brain, as opposed to being within a ventricle of the brain.

A method within the scope of the present invention can be used to treat epilepsy, including: (1) focal (or partial) epilepsies, such as, benign occipital epilepsy (benign focal epilepsy with occipital paroxysms), benign rolandic epilepsy (benign focal epilepsy with centrotemporal spikes), frontal lobe epilepsy, occipital lobe epilepsy, mesial temporal lobe epilepsy and parietal lobe epilepsy; (2) generalized idiopathic epilepsies, such as benign myoclonic epilepsy in infants, juvenile myoclonic epilepsy, childhood absence epilepsy, juvenile absence epilepsy, and epilepsy with generalized tonic clonic seizures in childhood; (3) generalized symptomatic epilepsies, such as infantile spasms (West syndrome), Lennox-Gastaut syndrome and progressive myoclonus epilepsies, and; (4) unclassified epilepsies, such as febrile fits, epilepsy with continuous spike and waves in slow wave sleep (ESES), Landau Kleffner syndrome, Rasmussen's syndrome and epilepsy and inborn errors in metabolism A method for treating a movement disorder within the scope of the present invention can be by intracranial administration of a neurotoxin to a patient to thereby alleviate a symptom of the movement disorder. The neurotoxin is made by a bacterium selected from the group consisting of *Clostridium botulinum*, *Clostridium butyricum* and *Clostridium beratti*, or can be expressed by a suitable host (i.e. a recombinantly altered *E. coli*) which encodes for a neurotoxin made by *Clostridium botulinum*, *Clostridium butyricum* or *Clostridium beratti*. Preferably, the neurotoxin is a botulinum toxin, such as a botulinum toxin type A, B, $C_1$, D, E, F and G.

The neurotoxin can be administered to various brain areas for therapeutic treatment of a movement disorder, including to a lower brain region, to a pontine region, to a mesopontine region, to a globus pallidus and/or to a thalamic region of the brain.

The neurotoxin can be a modified neurotoxin, that is a neurotoxin which has at least one of its amino acids deleted, modified or replaced, as compared to a native or the modified neurotoxin can be a recombinant produced neurotoxin or a derivative or fragment thereof.

Intracranial administration of a neurotoxin according to the present invention can include the step of implantation of controlled release botulinum toxin system. A detailed embodiment of the present invention can be a method for treating a movement disorder by intracranial administration of a therapeutically effective amount of a botulinum toxin to a patient to thereby treating a symptom of a movement disorder. The movement disorders treated can include Parkinson's disease, Huntington's Chorea, progressive supranuclear palsy, Wilson's disease, Tourette's syndrome, epilepsy, chronic tremor, tics, dystonias and spasticity A further embodiment within the scope of the present invention can be a method for treating epilepsy, the method comprising the steps of: selecting a neurotoxin with tremor suppressant activity; choosing an intracranial target tissue which influences a movement disorder; and; intracranially administering to the target tissue a therapeutically effective amount of the neurotoxin selected, thereby treating the epilepsy.

Thus, a method for treating an epilepsy according to the present invention can have the step of intracranial administration of a neurotoxin to a mammal, thereby alleviating a symptom of an epilepsy experienced by the mammal. Most preferably, the botulinum toxin used is botulinum toxin type A because of the high potency, ready availability and long history of clinical use of botulinum toxin type A to treat various disorders.

We have surprisingly found that a botulinum toxin, such as botulinum toxin type A, can be intracranially administered in amounts between about $10^{-3}$ U/kg and about 10 U/kg to alleviate a focal epilepsy disorder experienced by a human patient. Preferably, the botulinum toxin used is intracranially administered in an amount of between about $10^{-2}$ U/kg and about 1 U/kg. More preferably, the botulinum toxin is administered in an amount of between about $10^{-1}$ U/kg and about 1 U/kg. Most preferably, the botulinum toxin is administered in an amount of between about 0.1 unit and about 5 units. Significantly, the movement disorder alleviating effect of the present disclosed methods can persist for between about 2 months to about 6 months when administration is of aqueous solution of the neurotoxin, and for up to about five years when the neurotoxin is administered as a controlled release implant.

A further preferred method within the scope of the present invention is a method for treating a movement disorder by selecting a neurotoxin with tremor suppressant activity, choosing an intracranial target tissue which influences a movement disorder; and intracranially administering to the target tissue a therapeutically effective amount of the neurotoxin selected.

Another preferred method within the scope of the present invention is a method for improving patient function, the method comprising the step of intracranially administering a neurotoxin to a patient, thereby improving patient function as determined by improvement in one or more of the factors of reduced pain, reduced time spent in bed, increased ambulation, healthier attitude and a more varied lifestyle.

The present invention encompasses a method for treating epilepsy. The method can comprise the step of intracranial administration of a botulinum toxin to an epileptogenic focus a patient, thereby treating epilepsy. The botulinum toxin is a botulinum toxin types A, B, C, D, E, F or G. Preferably, the botulinum toxin is administered in an amount of between about $10^{-3}$ U/kg and about 100 U/kg of patient weight. This method can alleviate epilepsy for between about 1 month and about 5 years. The botulinum toxin can be administered to a lower brain region, pontine region, mesopontine region, globus pallidus or to a thalamic region of a brain of a patient.

The intracranial administration step can comprise implantation of a controlled release botulinum toxin system. A detailed embodiment of the disclosed method can comprise the step of intracranial administration of a therapeutically effective amount of a botulinum toxin type A to an epileptogenic focus of a patient, thereby treating epilepsy.

A particular detailed method for treating epilepsy according to the present invention can comprise the step of intracranial administration of a therapeutically effective amount of a botulinum toxin to a epileptogenic focus of a patient located in a thalamus of the patient between 3 to 6 mm posterior to the mid anterior commissure-posterior commissure plane, 12 mm to 16 mm lateral to the mid anterior commissure-posterior commissure plane, and 0 to 3 mm above the level of the mid anterior commissure-posterior commissure plane, thereby treating epilepsy.

DRAWINGS

Figure 7:
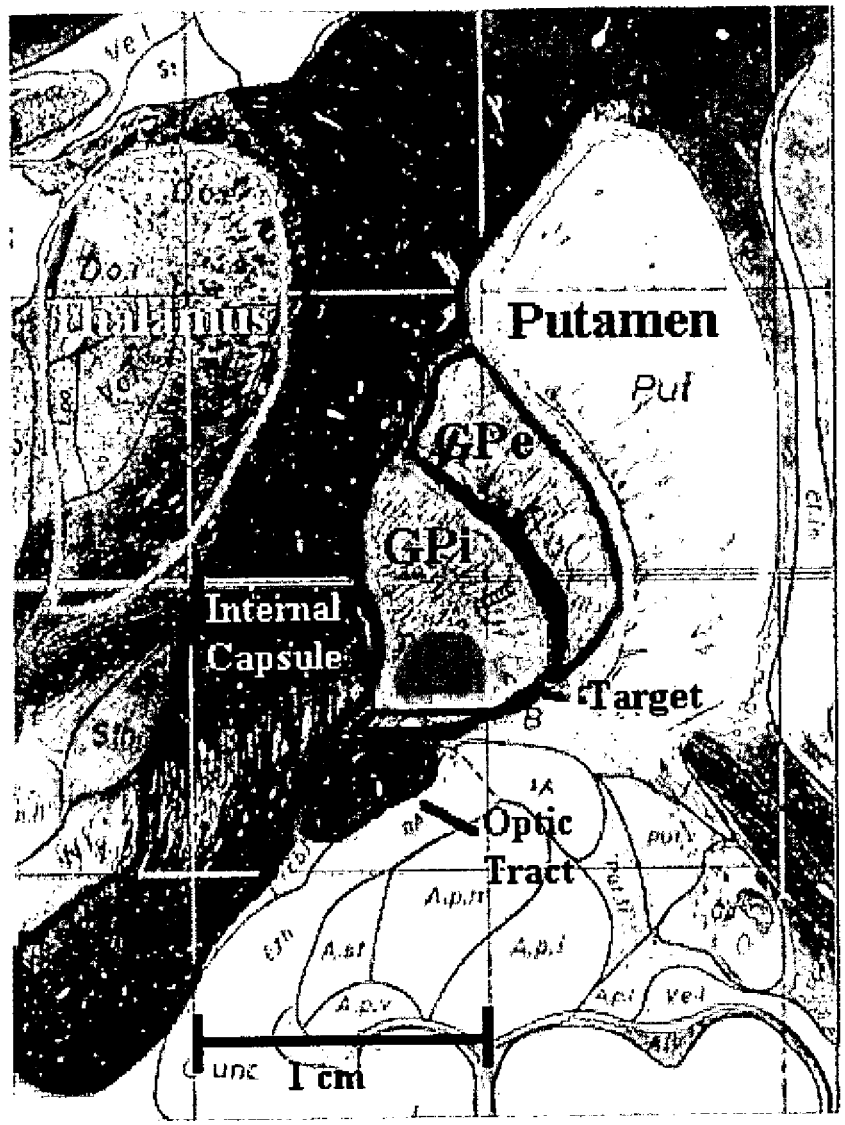

FIG. 7 is a coronal image of the brain, the plane (cut) is from the top of the head to the bottom. The axons are stained black, and the neurons are unstained. Illustrated is the putamen, globus pallidus externus, globus pallidus internus and these structures are lateral to the internal capsule. Directly below the globus pallidus internus is the optic tract.

DESCRIPTION

The present invention is based upon the discovery that local (i.e. intracranial) administration (as through stereotactic delivery) of a botulinum toxin (native or modified) can reduce excess electrical activity (i.e. reduction of hyperexcitability) of an epileptic focus in the brain, thereby treating epilepsy. As set forth herein, stereotactic methodologies permit precise therapeutic delivery of bioactive botulinum toxin into specific epileptic foci for the treatment of epilepsy.

A method within the scope of the present invention is primarily a treatment for intractable seizures, i.e. where surgery is indicated. We have surprising discovered that intracranial administration of a botulinum toxin to aberrant tissue within an identified epileptogenic focus can be used to treat epilepsy. An intractable seizure means that the seizures have failed reasonable attempts at medical (drug control). Significantly, use of a botulinum toxin, unlike surgical resection, to cause a "chemical ectomy", as described herein does not cause irreversible damage to the target neurons.

A method within the scope of the present invention can be used to treat a focal epilepsy as a focal epilepsy results from a localized lesion (a "focus") of functional abnormality. EEG can be used to localize abnormal spiking waves of a target focus followed by intracranial administration of a botulinum toxin to non-surgically (i.e. no tissue resection or ablation is carried out) downregulate the identified hyperexcitable focus.

Botulinum toxin is too large to cross the blood brain barrier and therefore cannot be given systemically to treat an intracranial epileptogenic brain focus. Additionally, systemic administration of a botulinum toxin can be expected to result in symptoms of botulism and possibly death.

Without wishing to be bound by theory, a proposed physiological mechanism for the efficacy of a method within the scope of our invention can be as follows. It is hypothesized that localized delivery of a botulinum toxin (such as a botulinum toxin type A) into or in the vicinity of an active epileptic focus (or foci) disrupts the hyperexcitability of the focus thereby suppressing or limiting seizure propagation.

The specific actions of a botulinum toxin on presynaptic nerve terminals are well characterized at the neuromuscular junction. Briefly, botulinum toxin binds to the presynaptic cholinergic terminals through interactions of its heavy chain binding domain with an, as yet, unspecified membrane receptor complex; gains entry through endocytosis that is independent of vesicular recycling mechanisms; undergoes a pH-dependent conformational shift within the endosomal vesicle that results in the translocation of the enzymatically active light chain to the cytosol; blocks vesicular neurotransmitter release by cleaving the C-termini of SNAP-25 proteins involved in vesicle docking. Although botulinum toxin actions in the periphery are selective for cholinergic neurons of the neuromuscular junction, experimental evidence suggests that the toxin is relatively non-selective in exerting actions on mammalian central nervous system neurons. Thus, botulinum toxin inhibits neurotransmitter release from particulate preparations of brain and spinal cord (Bigalke H., et al., *Tetanus toxin and botulinum A toxin inhibit release and uptake of various transmitters, as studied with particulate preparations from rat brain and spinal cord*, Naunyn Schmiedebergs Arch Pharmacol 1981 June; 316(3):244-51) and blocks presynaptic vesicle exocytosis in primary neuronal cultures from hippocampus (Owe-Larsson B., et al., *Distinct effects of clostridial toxins on activity-dependent modulation of autaptic responses in cultured hippocampal neurons*, Eur J Neurosci 1997 August; 9(8):1773-7; Trudeau L. et al., *Modulation of an early step in the secretory machinery in hippocampal nerve terminals*, Proc Natl Acad Sci USA 1988 Jun. 9; 95(12):7163-8) and spinal cord (Bigalke H., et al., Botulinum A neurotoxin inhibits non-cholinergic synaptic transmission in mouse spinal cord neurons in culture, Brain Res 1985 Dec. 23; 360(1-2):318-24).

While botulinum toxin has been shown to target presynaptic terminals, the toxin may be able to exert postsynaptic actions as well. Activation of the metabotropic glutamate receptor 1 (mGluR1) has been shown to potentiate N-methyl-D-aspartate (NMDA) receptor-mediated postsynaptic responses, and NMDA receptor-mediated responses have been implicated in mechanisms of synaptic plasticity and in learning and memory. It has demonstrated that the potentiation of NMDA responses by mGluR1 activation is due to an enhanced delivery of new NMDA receptors to the postsynaptic cell surface, through regulated vesicular exocytosis (Lan J., et al., *Activation of metabotropic glutamate receptor 1 accelerates NMDA receptor trafficking*: J Neurosci 2001 Aug. 15; 21(16):6058-68). Lan et al further demonstrated that the light chain of botulinum toxin type A attenuates the potentiating actions of mGlu1 receptor activation on NMDA receptor responses. Thus, botulinum toxin type A administration can potentially effect both pre- and post-synaptic responses. As noted earlier, blockade or inhibition of presynaptic vesicular release at excitatory synapses blocks neurotransmission and produces desynchronization of network activity, such as in the epileptogenic hippocampus, and leads to changes in synaptic plasticity (LTP). Thus, through inhibitory actions on synaptic vesicular release, a botulinum toxin can produce, at least in part, a denervation of the neural network within the treated focus, leading to a "functional (chemically induced) resection", suppression of focal hyperexcitability and lasting changes in synaptic plasticity. At the same time it is significant to note that, axons coursing through the target structure without synapsing would be spared. Thus, because endocytotic processes have been characterized at presynaptic terminals and somatodendritic cell surfaces and are negligible or absent along axons (Huttner W., et al., *Exocytotic and endocytotic membrane traffic in neurons*, Curr Opin Neurobiol 1991 October; 1(3):388-92; Parton R., et al., *Cell biology of neuronal endocytosis*, J Neurosci Res 1993 Sep. 1; 36(1):1-9. and because botulinum toxin entry into neurons is mediated through endocytosis, the toxin would not be expected to enter axons, arising from cell bodies in distant nuclei, that are strictly coursing through, but not synapsing within, the injected focus.

The reduction of focal hyperactivity will, expectedly, disrupt the pathological recruitment of downstream neuronal paths, resulting in a suppression of seizure propagation and yielding a desired anticonvulsant/antiepileptic effect. This outcome is based upon our current understanding of neuroanatomical circuitry and mechanisms of seizure propagation. In all models of cortical (and hippocampal) epileptogenesis, seizure generation and propagation is dependent upon neurotransmission (McCormick D. A., et al., *On the cellular and network bases of epileptic seizures*, Annu Rev Physiol 63: 815-46; 2001). Thus, inhibition of neurotransmission within a focus would lead to inhibition of signal transmission to target cell populations outside of the focus, and concomitant activity-dependent reduction in hyperexcitability. Additionally, there would be a reduction in ephaptic neuronal recruitment, due to a reduction in activity-dependent field effects, resulting in decreased neuronal synchronization in perifocal tissues. Burst discharges are sensitive to inhibition resulting from the depletion of the readily-releasable vesicle pool in presynaptic terminals, as has been demonstrated in the hippocampus (Staley et al 1998, Ibid). Thus, burst discharges arising from a targeted focus would be subject to similar inhibition upon botulinum toxin administration, since blockade of vesicular release produces a functional effect similar to depletion of the readily-releasable vesicular pool.

Botulinum toxin injection into a epileptogenic focus can be viewed as an adjunct or alternative to resective surgery, depending upon the observed characteristics of the underlying hyperexcitable tissue upon localization and examination. As well, intrafocal toxin injection can be supplemented with standard AED pharmacotherapy postoperatively, to suppress residual seizure activity while allowing for the toxin effect to occur.

It has been reported that "Since the thalamus and the cortex are strongly innervated by cholinergic neurons projecting from the brainstem and basal forebrain, an imbalance between excitation and inhibition, brought about by the presence of mutant (neuronal nicotinic acetylcholine) receptors (which display an increased acetylcholine sensitivity) could generate seizures by facilitating and synchronizing spontaneous oscillations in thalmo-cortical circuits." Raggenbass M., et al., *Nicotinic receptors in circuit excitability and epilepsy*, J Neurobiol. 2002 December; 53(4): 580-9. This publication clearly supports the proposed efficacy of the present invention.

Intracranial administration of a botulinum toxin downregulates hyperexcitable neurons in an epileptogenic focus and can provide a cure for epilepsy due to synaptic plasticity which results in a "rewiring" of neuronal circuitry as new neuronal circuits are established to bypass the chemically deactivated epileptogenic focus.

Focal application of botulinum toxin can be used to treat many indications, such as focal, generalized idiopathic, generalized symptomatic, and unclassified epilepsies.

Thus, the present invention is based on the discovery that significant and long lasting relief from a variety of different movement disorders can be achieved by intracranial administration of a neurotoxin. Intracranial administration permits the blood brain barrier to be bypassed and delivers much more toxin to the brain than is possible by a systemic route of administration. Furthermore, systemic administration of a neurotoxin, such as a botulinum toxin, is contraindicated due to the severe complications (i.e. botulism) which can result from entry of a botulinum toxin into the general circulation. Additionally, since botulinum toxin does not penetrate the blood brain barrier to any significant extent, systemic administration of a botulinum toxin has no practical application to treat an intracranial target tissue.

The present invention encompasses any suitable method for intracranial administration of a neurotoxin to a selected target tissue, including injection of an aqueous solution of a neurotoxin and implantation of a controlled release system, such as a neurotoxin incorporating polymeric implant at the selected target site. Use of a controlled release implant reduces the need for repeat injections.

Intracranial implants are known. For example, brachytherapy for malignant gliomas can include stereotactically implanted, temporary, iodine-125 interstitial catheters. Scharfen. C. O., et al., *High Activity Iodine-125 Interstitial Implant For Gliomas*, Int. J. Radiation Oncology Biol Phys 24(4); 583-591:1992. Additionally, permanent, intracranial, low dose $^{125}$I seeded catheter implants have been used to treat brain tumors. Gaspar, et al., *Permanent $^{125}$I Implants for Recurrent Malignant Gliomas*, Int J Radiation Oncology Biol Phys 43(5); 977-982:1999. See also chapter 66, pages 577-580, Bellezza D., et al., *Stereotactic Interstitial Brachytherapy*, in Gildenberg P. L. et al., *Textbook of Stereotactic and Functional Neurosurgery*, McGraw-Hill (1998).

Furthermore, local administration of an anti cancer drug to treat malignant gliomas by interstitial chemotherapy using surgically implanted, biodegradable implants is known. For example, intracranial administration of 3-bis(chloro-ethyl)-1-nitrosourea (BCNU) (Carmustine) containing polyanhydride wafers, has found therapeutic application. Brem, H. et al., *The Safety of Interstitial Chemotherapy with BCNU-Loaded Polymer Followed by Radiation Therapy in the Treatment of Newly Diagnosed Malignant Gliomas: Phase I Trial*, J Neuro-Oncology 26:111-123:1995.

A polyanhydride polymer, GLIADEL® (Stolle R & D, Inc., Cincinnati, Ohio, (a copolymer of poly-carboxyphenoxypropane and sebacic acid in a ratio of 20:80), has been used to make implants, intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Inrraoperative Controlled Delivery by Biodegradable Polymers of Chemotherapy for Recurrent Gliomas*, Lancet 345; 1008-1012:1995.

An implant can be prepared by mixing a desired amount of a stabilized neurotoxin (such as non-reconstituted BOTOX®) into a solution of a suitable polymer dissolved in methylene chloride, at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Diffusion of biological activity of a botulinum toxin within a tissue appears to be a function of dose and can be graduated. Jankovic J., et al *Therapy With Botulinum Toxin*, Marcel Dekker, Inc., (1994), page 150.

Local, intracranial delivery of a neurotoxin, such as a botulinum toxin, can provide a high, local therapeutic level of the toxin and can significantly prevent the occurrence of any systemic toxicity since many neurotoxins, such as the botulinum toxins are too large to cross the blood brain barrier. A controlled release polymer capable of long term, local delivery of a neurotoxin to an intracranial site can circumvent the restrictions imposed by systemic toxicity and the blood brain barrier, and permit effective dosing of an intracranial target tissue. A suitable implant, as set forth in co-pending U.S. patent application Ser. No. 09/587,250 entitled "Neurotoxin Implant", allows the direct introduction of a chemotherapeutic agent to a brain target tissue via a controlled release polymer. The implant polymers used are preferably hydrophobic so as to protect the polymer incorporated neurotoxin from water induced decomposition until the toxin is released into the target tissue environment.

Local intracranial administration of a botulinum toxin, according to the present invention, by injection or implant to e.g. the cholinergic thalamus presents as a superior alternative to thalamotomy in the management of inter alia tremor associated with Parkinson's disease.

A method within the scope of the present invention includes stereotactic placement of a neurotoxin containing implant using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

Within wishing to be bound by theory, a further mechanism can be proposed for the therapeutic effects of a method practiced according to the present invention. Thus, a neurotoxin, such as a botulinum toxin, can inhibit neuronal exocytosis of several different CNS neurotransmitters, in particular acetylcholine. It is known that cholinergic neurons are present in the thalamus. Additionally, cholinergic nuclei exist in the basal ganglia or in the basal forebrain, with protections to motor and sensory cerebral regions. Thus, target tissues for a method within the scope of the present invention can include neurotoxin induced, reversible denervation of intracranial motor areas (such as the thalamus) as well as brain cholinergic systems themselves (such as basal nuclei) which project to the intracranial motor areas. For example, injection or implantation of a neurotoxin to a cholinergically innervated thalamic nuclei (such as Vim) can result in (1) downregulation of Vim activity due to the action of the toxin upon cholinergic terminals projecting into the thalamus from basal ganglia, and; (2) attenuation of thalamic output due to the action of the toxin upon thalamic somata, both cholinergic and non-cholinergic, thereby producing a chemical thalamotomy.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection. Botulinum toxin type B is a less preferred neurotoxin to use in the practice of the disclosed methods because type B is known to have a significantly lower potency and efficacy as compared, to type A, is not readily available, and has a limited history of clinical use in humans. Furthermore, the higher protein load with regard to type B can cause immunogenic reaction to occur with development of antibodies to the type B neurotoxin.

The amount of a neurotoxin selected for intracranial administration to a target tissue according to the present disclosed invention can be varied based upon criteria such as the movement disorder being treated, its severity, the extent of brain tissue involvement or to be treated, solubility characteristics of the neurotoxin toxin chosen as well as the age, sex, weight and health of the patient. For example, the extent of the area of brain tissue influenced is believed to be proportional to the volume of neurotoxin injected, while the quantity of the tremor suppressant effect is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

We have found that a neurotoxin, such as a botulinum toxin, can be intracranially administered according to the present disclosed methods in amounts of between about $10^{-3}$ U/kg to about 10 U/kg. A dose of about $10^{-3}$ U/kg can result in an epileptic tremor suppressant effect if delivered to a small intracranial nuclei. Intracranial administration of less than about $10^{-3}$ U/kg does not result in a significant or lasting therapeutic result. An intracranial dose of more than 10 U/kg of a neurotoxin, such as a botulinum toxin, poses a significant risk of denervation of sensory or desirable motor functions of neurons adjacent to the target.

A preferred range for intracranial administration of a botulinum toxin, such as botulinum toxin type A, so as to achieve a tremor suppressant effect in the patient treated is from about $10^{-2}$ U/kg to about 1 U/kg. Less than about $10^{-2}$ U/kg can result in a relatively minor, though still observable, tremor suppressant effect. A more preferred range for intracranial administration of a botulinum toxin, such as botulinum toxin type A, so as to achieve an antinociceptive effect in the patient treated is from about $10^{-1}$ U/kg to about 1 U/kg. Less than about $10^{-1}$ U/kg can result in the desired therapeutic effect being of less than the optimal or longest possible duration. A most preferred range for intracranial administration of a botulinum toxin, such as botulinum toxin type A, so as to achieve a desired tremor suppressant effect in the patient treated is from about 0.1 units to about 100 units. Intracranial administration of a botulinum toxin, such as botulinum toxin type A, in this preferred range can provide dramatic therapeutic success.

The present invention includes within its scope the use of any neurotoxin which has a long duration tremor suppressant effect when locally applied intracranially to the patient. For example, neurotoxins made by any of the species of the toxin producing *Clostridium* bacteria, such as *Clostridium botulinum*, *Clostridium butyricum*, and *Clostridium beratti* can be used or adapted for use in the methods of the present invention. Additionally, all of the botulinum serotypes A, B, $C_1$, D, E, F and G can be advantageously used in the practice of the present invention, although type A is the most preferred and type B the least preferred serotype, as explained above. Practice of the present invention can provide a tremor suppressant effect, per injection, for 3 months or longer in humans.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, we have discovered that a surprisingly effective and long lasting treatment of a focal epilepsy can be achieved by intracranial administration of a neurotoxin to an afflicted patient. In its most preferred embodiment, the present invention is practiced by intracranial injection or implantation of botulinum toxin type A.

The present invention does include within its scope: (a) neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water.

EXAMPLES

The following examples set forth specific methods encompassed by the present invention to treat a movement disorder and are not intended to limit the scope of the invention.

Example 1

Intracranial Target Tissue Localization and Methodology

Stereotactic procedures can be used for precise intracranial administration of neurotoxin in aqueous form or as an implant to desired target tissue. Thus, intracranial administration of a neurotoxin to treat a drug resistant tremor (i.e. a resting tremor, such as can occur in Parkinson's disease, or an action tremor, such as essential tremor), multiple sclerosis tremors, post traumatic tremors, post hemiplegic tremors (post stroke spasticity), tremors associated with neuropathy, writing tremors and epilepsy can be carried out as follows.

A preliminary MRI scan of the patient can be carried out to obtain the length of the anterior commissure-posterior commissure line and its orientation to external bony landmarks. The base of the frame can then be aligned to the plane of the anterior commissure-posterior commissure line. CT guidance is used and can be supplemented with ventriculography. The posterior commissure can be visualized on 2-mm CT slices and used as a reference point. Where the target injection site is the basal part of the ventral intermedius nucleus of the ventrolateral thalamus, average coordinates are 6.5 mm anterior to the posterior commissure, 11 mm lateral to the third ventricular wall and 2 mm above the anterior commissure-posterior commissure line. This location is not expected to encroach on the sensory thalamus or on a subthalamic region.

Physiological corroboration of target tissue localization can be by use of high and low frequency stimulation through an electrode accompanying or incorporated into the long needle syringe used. A thermistor electrode 1.6 mm in diameter with a 2 mm exposed tip can be used (Radionics, Burlington, Mass.). With electrode high frequency stimulation (75 Hz) paraesthetic responses can be elicited in the forearm and hand at 0.5-1.0 V using a Radionics lesion generator (Radionics Radiofrequency Lesion Generator Model RFG3AV). At low frequency (5 Hz) activation or disruption of tremor in the affected limb occurred at 2-3 V. With the methods of the present invention, the electrode is not used to create a lesion. Following confirmation of target tissue localization, a neurotoxin can be injected, thereby causing a reversible, chemical thalamotomy. A typical injection is the desired number of units (i.e. about 0.1 to about 5 units of a botulinum toxin type A complex in about 0.1 ml to about 0.5 ml of water or saline. A low injection volume can be uses to minimize toxin diffusion away from target. Typically, the neurotransmitter release inhibition effect can be expected to wear off within about 2-4 months. Thus, an alternate neurotoxin format, neurotoxin incorporated within a polymeric implant, can be used to provide controlled, continuous release of therapeutic amount of the toxin at the desired location over a prolonged period.(i.e. from about 1 year to about 6 years), thereby obviating the need for repeated toxin injections.

Several methods can be used for stereotactically guided injection of a neurotoxin to various intracranial targets, such as the subthalamic nucleus (STN) for treatment of Parkinson's disease (Parkinson's disease). Thus a stereotactic magnetic resonance (MRI) method relying on three-dimensional (3D) T1-weighted images for surgical planning and multiplanar T2-weighted images for direct visualization of the STN, coupled with electrophysiological recording and injection guidance for unilateral or bilateral STN injection can be used. See e.g. Bejjani, B. P., et al., *Bilateral Subthalamic Stimulation for Parkinson's Disease by Using Three-Dimensional Stereotactic Magnetic Resonance Imaging and Electrophysiological Guidance*, J Neurosurg 92(4); 615-25: 2000. The STNs can be visualized as 3D ovoid biconvex hypointense structures located in the upper mesencephalon. The coordinates of the centers of the STNs can be determined with reference to the patient's anterior commissure-posterior commissure line by using as a landmark, the anterior border of the red nucleus.

Electrophysiological monitoring through several parallel tracks can be performed simultaneously to define the functional target accurately. Microelectrode recording can identify high-frequency, spontaneous, movement-related activity and tremor-related cells within the STNs. Neurotoxin injection into the STN can improve contralateral rigidity and akinesia and suppress tremor when present. The central track, which is directed at the predetermined target by using MRI imaging, can be selected for neurotoxin injection. No surgical complications are expected. The patient can show significantly improved parkinsonian motor disability in the "off" and "on" medication states and use of antiparkinsonian drug treatment can be dramatically reduced as is the severity of levodopa-induced dyskinesias and motor fluctuations.

Computer-aided atlas-based functional neurosurgery methodology can be used to accurately and precisely inject the desired neurotoxin or implant a neurotoxin controlled release implant. Such methodologies permit three-dimensional display and real-time manipulation of cerebral structures. Neurosurgical planning with mutually preregistered multiple brain atlases in all three orthogonal orientations is therefore possible and permits increased accuracy of target definition for neurotoxin injection or implantation, reduced time of the surgical procedure by decreasing the number of tracts, and facilitates planning of more sophisticated trajectories. See e.g. Nowinski W. L. et al., *Computer-Aided Stereotactic Functional Neurosurgery Enhanced by the Use of the Multiple Brain Atlas Database*, IEEE Trans Med Imaging 19(1); 62-69:2000.

Example 2

Treatment of Parkinson's Disease with Botulinum Toxin Type A

A 64 year old right-handed male presents with pronounced tremor of the extremities, bradykinesia, rigidity and postural changes such that he frequently falls. A prominent pill rolling tremor is noted in his right hand. Stroke is ruled out and it is noted that the symptoms are worse on his right side. Diagnosis of Parkinson's disease is made. Using CAT scan or MRI assisted stereotaxis, as set forth in Example 1 above, 2 units of a botulinum toxin type A (such as BOTOX® or about 8 units of DYSPORT®) is injected into the left side of the globus pallidus. The patient is discharged within 48 hours and with a few (1-7) days enjoys significant improvement of the parkinsonian motor symptoms more clearly on the right, but also on his left side. His dyskinesias almost completely disappear. The motor disorder symptoms of Parkinson's disease remain significantly alleviated for between about 2 to about 6 months. For extended therapeutic relief, one or more polymeric implants incorporating a suitable quantity of a botulinum toxin type A can be placed at the target tissue site.

Example 3

Treatment of Parkinson's Disease with Botulinum Toxin Type B

A 68 year left handed male presents with pronounced tremor of the extremities. bradykinesia, rigidity and postural changes such that he frequently falls. A prominent pill rolling tremor is noted on his left side. Stroke is ruled out and it is noted that the symptoms are worse on his left side. Diagnosis of Parkinson's disease is made. Using CAT scan or MRI assisted stereotaxis, as set forth in Example 1 above, from 10 to about 50 units of a botulinum toxin type B preparation (such as NEUROBLOC® or INERVATE®—both of which are a botulinum toxin type B preparataion is injected into the right side of the globus pallidus. The patient is discharged within 48 hours and with a few (1-7) days enjoys significant improvement of the parkinsonian motor symptoms more clearly on the left, but also on his right side. His dyskinesias almost completely disappear. The motor disorder symptoms of Parkinson's disease remain significantly alleviated for between about 2 to about 6 months. For extended therapeutic relief, one or more polymeric implants incorporating a suitable quantity of a botulinum toxin type B can be placed at the target tissue site.

Example 4

Treatment of Parkinson's Disease with Botulinum Toxin Types $C_1$-G

A female aged 71 is admitted with uncontrollable and frequent tremor. From 0.1 to 100 units of a botulinum toxin type $C_1$, D, E, F or G is injected unilaterally Into the ventrolateral thalamus for the disabling tremors. CAT scan or MRI assisted stereotaxis, as set forth in Example 1 above, supplemented by ventriculography is used. The patient is discharged within 48 hours and with a few (1-7) days enjoys significant remission of tremors which remain significantly alleviated for between about 2 to about 6 months. For extended therapeutic relief, one or more polymeric implants incorporating a suitable quantity of a botulinum toxin type $C_1$, D, E, F or G can be placed at the target tissue site.

Example 5

Treatment of Dystonia with Botulinum Toxin Type A

A 16 year old male child with severe, incapacitating dystonia, secondary to cranial trauma, affecting the proximal limb muscles is a candidate for unilateral thalamotomy on the left side, bilateral thalamotomy carrying a high risk of iatrogenic dysarthria and pseudubulbar effects. The patient has failed to respond or has become unresponsive to transcutaneous nerve stimulation, feedback display of the EMG and anticholinergics. The dystonia is relatively stable, the patient is sufficiently fit to withstand surgery and is significantly disabled with distal phasic and tonic limb dystonia.

A suitable stereotactic frame can be applied to the head with local anesthetic and ventriculography and stereotactic MRI can be performed. The stereotactic coordinates of the anterior commissure (AC) and the posterior commissure (PC) can be determined by using the computer software in the scanner. PC based software can be used to redraw the sagittal brain maps from the Schaltenbrand and Bailey and Schaltenbrand and Wahren atlases, stretched or shrunk as needed to the AC-PC distance of the patient and ruled in stereotactic coordinates for the actual application of the frame to the patient's head. The target sites are selected, their coordinates are read off and appropriate frame settings are made. A burr hole or twist drill hole can be made at or rostral to the coronal suture in the same sagittal plane as the target. This can facilitate plotting the physiological data used for target corroboration since the electrode trajectories traverse a single sagittal plane. The ventrocaudal nucleus of the thalamus (Vc) can be selected as a physiological landmark, lying 15 mm from the midline. The Vc can be easily recognized by recording individual tactile cells within it with their discrete receptive fields or by inducing paresthesias with stimulation in discreet projected fields.

A microelectrode recording needle (such a used for single fiber electromyographic recording having an approximately 25 micron diameter recording electrode) can be located within the bore of a microsyringe and is advanced toward the expected tactile representation of the fingers in the Vc and continuous recording is carried out to search for identifiable neurons. Microstimulation can be performed every millimeter, beginning about 10 mm above and extending to a variable distance below the target. If the first microelectrode trajectory enters, for example, the tactile representation of the lips of a patient with upper limb dystonia, a second trajectory can be carried out 2 mm more lateral. Upon encountering lower limb responses, the next trajectory can be made 2 mm more medial. Once the tactile representation of the hand is found, the next trajectory can be made 2 mm rostral to it, where recording reveals kinesthetic neurons that respond to bending of specific contralateral joints or pressure on specific contralateral sites. If dystonia is confined to the leg, the process described above can be aimed at the thalamic representation for the leg.

Upon microstimulation localization of the stereotactically MRI guided recording/stimulating needle electrode to the target, a neurotoxin implant can be injected. The implant can comprise a neurotoxin, such as a of botulinum toxin type A, incorporated within biodegradable polymeric microspheres or a biodegradable pellet, either implant format containing about 20 total units (about 1 ng) of the toxin with implant characteristics of continuous release over a period of at least about four years of a therapeutic level of the toxin at point of the implant release site and for a radius of about 2-3 mm on each side o the target site. The implant can release about 1 unit of toxin essentially immediately and further amounts of about one unit cumulatively over subsequent 2-4 months periods.

The patient's dystonic contractions can subside almost immediately, and can remain substantially alleviated for between about 2 months to about 6 months per toxin injection or for between about 1 to 5 years depending upon the particular release characteristics of the implant polymer and the quantity of neurotoxin loaded therein.

Example 6

Treatment of Dystonia with Botulinum Toxin Types B-G

The patient of example 5 above can be equivalently treated using the same protocol and approach to target with between about 1 unit and about 1000 units of a botulinum toxin type B, $C_1$, D, E, F or G in aqueous solution or in the form of a suitable neurotoxin implant. With such a treatment, the dystonic contractions subside within 1-7 days, and remain substantially alleviated for between about 2-6 months per toxin injection or for between about 1 to 5 years depending upon the particular release characteristics of the implant polymer and the quantity of neurotoxin loaded therein.

Example 7

Treatment of Tremor with Botulinum Toxin Type A

A 44 year old male presents with severe incapacitating tremor of three years duration which disrupts his activities of daily living. There is also asymmetry of the motor symptoms between the two side of the body and levodopa has induced dyskinesia in the extremities. Tremor cells are identified by stereotactic examination of the effect upon the tremor by electrical stimulation of the proposed target cell. The effect of stimulation is noted to inhibit the tremor. Stereotactic guided (as in Example 1) implant placement can be made at a site about 14 to 15 mm from the midline and 2-3 mm above the AC-PC line in the middle of kinesthetic and/or voluntary tremor cells. The target site can be the VL or Vi.

The implant can be either an aqueous solution of botulinum toxin type A incorporated within biodegradable polymeric microspheres or botulinum toxin type A biodegradable pellet, either implant format containing about 20 total units (about 1 ng) of the toxin with implant characteristics of continuous release over a period of at least about four years of a therapeutic level of the toxin at point of the implant release site and in about 2-3 mm on each side. The implant can release about 1 unit of toxin essentially immediately and further amounts of about one unit cumulatively over subsequent 2-4 months periods.

The patient's tremors can subside within 1-7 days, and can remain substantially alleviated for between about 2 months to about 6 months per toxin injection or for between about 1 to 5 years depending upon the particular release characteristics of the implant polymer and the quantity of neurotoxin loaded therein. Notably, there can be significant attenuation of distal limb movements, both phasic and tonic on the right side.

Example 8

Treatment of Tremor with Botulinum Toxin Types B-G

The patient of example 7 above can be equivalently treated using the same protocol and approach to target with between about 1 unit and about 1000 units of a botulinum toxin type B, $C_1$, D, E, F or G in aqueous solution or in the form of a suitable neurotoxin implant. With such a treatment, the tremors can subside within 1-7 days, and can remain substantially alleviated for between about 2-6 months per toxin injection or for between about 1 to 5 years depending upon the particular release characteristics of the implant polymer and the quantity of neurotoxin loaded therein.

Example 9

Treatment of Epilepsy with Botulinum Toxin Type A

A right handed, female patient age 22 presents with a history of epilepsy. Based upon MRI and a study of EEG recording, a diagnosis of temporal lobe epilepsy is made. An implant which provides about 5-50 units of a neurotoxin (such as a botulinum toxin type A) can be inserted at (or alternately 1-10 units of a botulinum toxin type A aqueous solution [less than 0.1 milliliter volume] can be infused or injected into) an identified epileptogenic focus located in the anterior part of the temporal lobe, 5-6 cm from the tip of the lobe along the middle temporal gyrus with a unilateral approach to the nondominant, left hemisphere. The epileptic seizures can be substantially reduced almost immediately, and remain substantially alleviated thereafter.

Administration of the botulinum toxin is carried out so as to reduce the likelihood of dosing non-epileptized cerebral tissues. Thus, toxin administration is not to tissues outside the target focus in the temporal lobe where the ictal discharges responsible for the seizures are localized. This can be carried out by respecting certain anatomic landmarks to thereby avoid visual and language disorders so that dosing spares temporal language cortical region and optic radiations. Hence, the posterior limits for dosing (i.e. for the extent of the chemical lobectomy caused by the botulinum toxin) is 5-6 cm from the tip of the lobe along the middle temporal gyrus when operating on the nondominant hemisphere, and 4-4.5 cm on the dominant side. Additionally, only the first 2 cm of the superior gyrus are within the toxin dose field.

Example 10

Treatment of Epilepsy with Botulinum Toxin Types B-G

The patient of example 9 above or in examples 11-20 can be equivalently treated using the same protocol and approach to target with between about 1 unit and about 1000 units of a botulinum toxin type B, $C_1$, D, E, F or G in aqueous solution or in the form of a suitable neurotoxin implant. With such a treatment, the epileptic seizures subside within a few minutes or hours and can remain substantially alleviated thereafter.

It is concluded that neurotoxin injection or implantation of a controlled release neurotoxin implant according to the methods of the present invention, with the aid of 3D MR imaging and electrophysiological guidance, can be a safe and effective therapy for patients suffering from various movement disorders, such as severe, advanced non-AED responsive epilepsy. Suitable patients include those who have become largely if not entirely refractory to chemotherapy prior to intracranial neurotoxin administration as set forth herein.

Example 11

Treatment of Epilepsy by Administration of a Botulinum Toxin to an Epileptogenic Focus Located in the Thalamus A 34 year old male patient present with intractable epilepsy and frequent limb tremors. To identify an abnormal area of cortex from which the seizures originate a noninvasive, presurgical evaluation is conducted with the patient's consent, comprising the taking of a detailed clinical history, followed by a physical examination, neuro-imaging (magnetic resonance imaging (MRI), functional imaging to visualize alterations in cerebral metabolism using Positron Emission Tomography (PET), and Single Photon Emission Computerized Tomography (SPECT)), 24 hour intensive video-EEG monitoring, neuropsychological testing and assessment of psychosocial functioning.

The evaluation locates a focal origin of the seizures, as a primary epileptogenic region. Standard preoperative blood tests are performed with special attention to platelets, bleeding time, PT and PTT. The patients is advised to discontinue aspirin and other non-steroidal anti-inflammatory agents at least 5 days prior to surgery. The patient begins a fast the evening before surgery.

The toxin induced thalamotomy is performed under local anesthesia and requires the full cooperation of the patient therefore the intraoperative use of sedating agents is avoided. Intravenous access is established ipsilateral to the planned botulinum toxin induced thalamotomy to allow complete freedom of movement in the extremity of interest and oxygen is supplied by nasal cannula. EKG, pulse oximetry and BP is monitored but an arterial line is not inserted. Blood pressure is maintained in the normal range for the patient. Bladder catheterization is not performed.

An MRI compatible stereotactic frame is affixed to the cranial vault after infiltration of the pin insertion sites with 1% lidocaine with 1/200,000 epinephrine he pin insertion sites are chosen to avoid artifact through the planned axial imaging sections of interest. The frame (illustrated by FIG. 1) is placed as symmetrically as possible on the head to minimize rotation and lateral tilt. This ensures that any changes made in electrode position intraoperatively are entirely in the planned direction. The instrument used is the CRW frame (Radionics, Burlington, Mass.).

Following frame placement (as illustrated by FIG. 2), the patient is taken to the MRI scanner where sagittal T1-weighted images are obtained first. These images are used to identify the anterior commissure (AC) and the posterior commissure (PC) and to measure the AC-PC length. Next T1-weighted (TR 400, TE 12/Fr, FOV 30×30, 2 NEX, 3 mm thickness) axial images are obtained through the basal ganglia so that these images are parallel to the AC-PC plane. Additional images in the coronal plane with fast spin echo inversion (FSE IR) recovery sequences to accentuate the gray-white matter borders of the thalamus and internal capsule are also used. The spatial accuracy of the stereotactic frame in the scanner is verified with phantoms.

Stereotactic CT imaging is also carried out to enhance targeting accuracy. Thus, after MR imaging, the patient is taken to the CT scanner and after the appropriate localizer is placed, and axial CT images (DFOV, 1.0-1.5 mm thickness) roughly parallel to the intercommissural line and through the area of interest are obtained. The AC/PC line is identified and used for initial target identification.

The target focus is located at a point 4 to 5 mm posterior to the mid anterior commissure-posterior commissure (AC-PC) plane, 13.5 to 15 mm lateral to the midline, and 0 to 1 mm above the level of the intercommisural plane. When the third ventricle is dilated, we add 1-2 mm to the lateral dimension.

Once the target point has been calculated, the patient is brought to the operating room. A single dose of an appropriate prophylactic antibiotic is given. The patient is placed in a comfortable position (FIG. 3) and the frame is fixed to the operating table with the head only slightly elevated above the chest to avoid air embolism. A small patch of hair is shaved over the appropriate frontal region and the area is then prepared and draped. After infiltration of the scalp with 1% lidocaine with 1/200,000 epinephrine, a 2.5 cm parasagittal incision (FIG. 4) is made and a burr hole placed 2.0 cm from the midline at the level of the coronal suture. The dura is coagulated and opened and a small pial incision made, so that the dura is opened to expose the temporal tip and a small portion of the suprasylvian cortex (FIG. 5). Cortical veins are avoided to permit atraumatic introduction of the electrode. At this point the stereotactic arc is brought into the target position and the electrode guide tube is lowered into the burr hole directly over the pial incision. The skin is then temporarily closed around the guide tube with nylon sutures to prevent excessive loss of CSF and brain settling.

Since there are individual differences in thalamic anatomy, initial target selection is only approximate and final targeting is performed using micro-electrode recordings, and macrostimulation. The initial pass is performed with a micro-electrode to obtain spontaneous neurophysiologic data and then this is followed by the macrostimulation/lesioning electrode. True microelectrodes are used (made of tungsten), which allow for the discrimination of single neurons. The electrodes are connected via short leads to a preamplifier. The signal from the preamplifier is then filtered, amplified, and passed through a window discriminator.

Microelectrode recordings in the ventrolateral thalamus reflect the connectivity of the various nuclei. Recordings in the Vop nucleus reveals voluntary cells that are less noisy than those in Vim (ventrointermedius nucleus of the thalamus) or VC (ventrocaudalis). These cells change their firing rate in advance or at the beginning of their related movements. Other cells may increase their firing shortly before the movement while others may show a decreased rate or become rhythmic at the onset or completion of a movement. Recordings in Vim reveal moderately noisy high voltage neurons which respond to contralateral passive joint movement, squeezing of muscle bellies, or pressure on deep structures such as tendons. This patient has tremors and kinesthetic cells fire rhythmically at the tremor frequency. Microelectrode recordings in VC reveal very noisy spontaneous activity and many high voltage cells. These cells respond to superficial light tough such as light brushing of the skin or a puff of air. The cells respond faithfully without fatigue. The largest volume of VC is occupied by tactile cells representing the face and manual digits. The floor of the thalamus is difficult to discern but is identified by the sudden loss of spontaneous neuronal activity as the microelectrode leaves the gray matter of the thalamus and enters the white matter of the zona incerta. Careful analysis of the neuronal activity of these various cell types confirms that the appropriate target in Vim thalamus is selected.

Macrostimulation is also used to delineate the optimal location for toxin administration. A commercially available lesion generator (Radionics, Burlington, Mass.), is used for impedance monitoring, stimulation, but is not used for lesioning. Based on the stereotactic coordinates, a side-seeking (SSE) macroelectrode (Radionics, Burlington, Mass.) with a 4 mm×1.8 mm uninsulated tip is introduced under impedance monitoring. The impedance drops by about 100 when the gray matter of the basal ganglia/thalamus is reached. Within the electrode tip is a much smaller electrode (2 mm×0.5 mm) that can be extruded in small increments so that without moving the parent electrode shaft, exploration medially, laterally and posteriorly at any angle is possible. It is through this smaller electrode that stimulation is performed. Stimulation is performed with square wave pulses at 0.5 to 2.0 volts with a frequency of 2 Hz to obtain motor thresholds and at 50 to 75 Hz to assess for amelioration of symptoms or sensory responses. A botulinum toxin type A can be injected into the target tissue through a stereotactically placed 30 gauge stainless steel tube using the method set forth by Levy R., et al., *Lidocaine and muscimol microinjections in subthalamic nucleus reverse parkinsonian symptoms*, Brain (2001), 124, 2105-2118. Thus, the injection cannula can be connected to a 10-15 cm piece of polyethylene tubing with a inside diameter of 0.58 mm and sealed with epoxy glue. The aqueous toxin can be preloaded in the cannula and polyethylene tubing.

The toxin induced thalamotomy target is the Vim nucleus and occasionally, the mere introduction of the electrode can reduce an epileptic tremor indicating that the electrode is in good position. More often, due to individual variation and the small size of Vim, the electrode can be in a suboptimal position and require adjustment. Our goal is to place toxin within Vim, directly anterior to the appropriate somatotopic area in VC and medial to the internal capsule without encroaching on either structure. Fortunately, intraoperative stimulation and microelectrode recording allows for differentiation of the internal capsule, Vop (ventraloralis posterior nucleus), Vim and VC nuclei based on their physiologic responses. If the electrode is placed too anteriorly in the Vop nucleus, low frequency stimulation can induce movement in the contralateral limbs. This movement is focal at threshold, beginning at one joint and involving greater parts of the contralateral limbs as stimulation intensity is increased.

Since Vim is thought to be the relay nucleus for kinesthetic sensation and VC the relay nucleus for superficial tactile sensation, high frequency stimulation can generally reflect this difference. Stimulation of the Vim usually elicits contralateral parasthesias at higher thresholds than those obtained in the VC nucleus. Vim stimulation can also induce a proprioceptive sensation that a contralateral limb is moving without any actual movement having taken place and may also induce peculiar sensations of vertigo, fainting, or dread but this is generally seen when the electrode is too inferior. It is important to distinguish Vim from VC for optimal catheter positioning. High frequency stimulation of the VC nucleus always causes contralateral parasthesias. However, the threshold (0.25-0.5 volts) for inducing parasthesias is usually much lower than that of the Vim nucleus. Consequently, low threshold parasthesias of the fingertips or mouth indicate that the electrode is too posterior and needs to be moved anteriorly. Sustained suprathreshold stimulation within VC may cause parasthesias that are unbearably intense. There is a clear medial-to-lateral somatotopy within VC with neurons representing the face most medial, those representing the lower limbs more lateral and those representing the upper extremity and hand intermediate. The definition of this somatotopic distribution is important as the toxin induced lesion in Vim should be made directly anterior to the appropriate site in the VC nucleus.

Another indication that the electrode is in good position relates to tremor response. Low frequency (2 Hz) stimulation within Vim usually causes driving of the tremor whereas high frequency (50 Hz) stimulation causes amelioration of the tremor. Suppression of epileptic tremor with 0.5-2.0 volts is the goal and indicates accurate targeting. In addition to the anterior-posterior differences between the nuclei, there is also a medial-to-lateral somatotopy within Vim. The face and mouth are represented most medially while the lower extremities are represented more laterally near the internal capsule. A botulinum toxin induced lesion is directed at the site corresponding to the most severe tremor. Lesions for tremor involving the upper extremity are placed slightly more medial than lesions for tremor involving the lower extremities. Use of the side exploring electrode allows for simplified exploration of this somatotopic organization because the electrode can be partially withdrawn, rotated, and reinserted thereby eliminating the need for complete repositioning.

Figure 1:
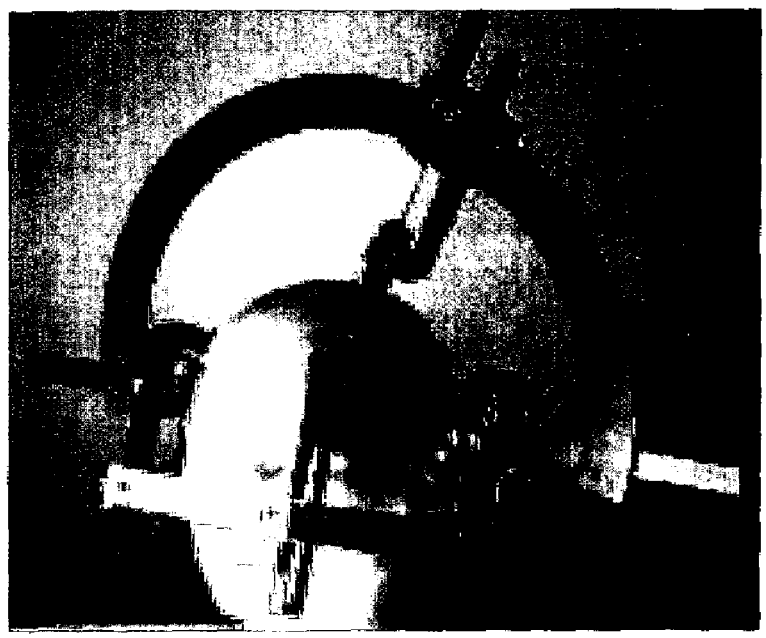
FIG. 1 illustrates preoperative placement of a frame based system for stereotactic neurosurgery for intracranial administration a botulinum toxin to a patent with epilepsy, according to the present invention.
Figure 2:
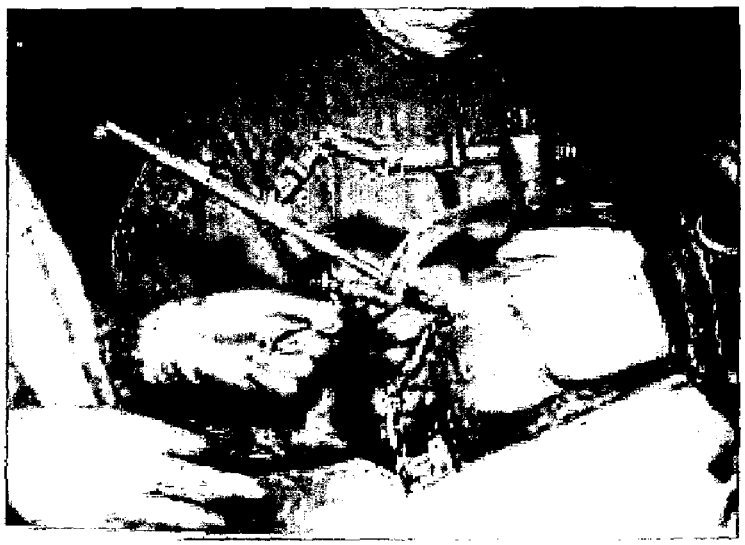
FIG. 2 illustrates initial intraoperative use of the system of FIG. 1.
Figure 3:
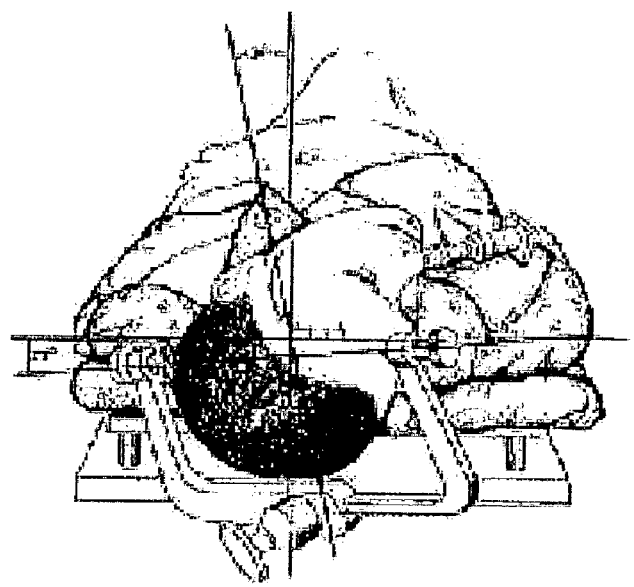
FIG. 3 Illustrates a method for positioning a patient for epilepsy surgery by temporal lobectomy induced upon stereotactic administration of a botulinum toxin to an epileptogenic focus in the temporal lobe of the patient. The head of the patient is angled so that the malar prominence is the highest portion of the patient's head.
Figure 4:
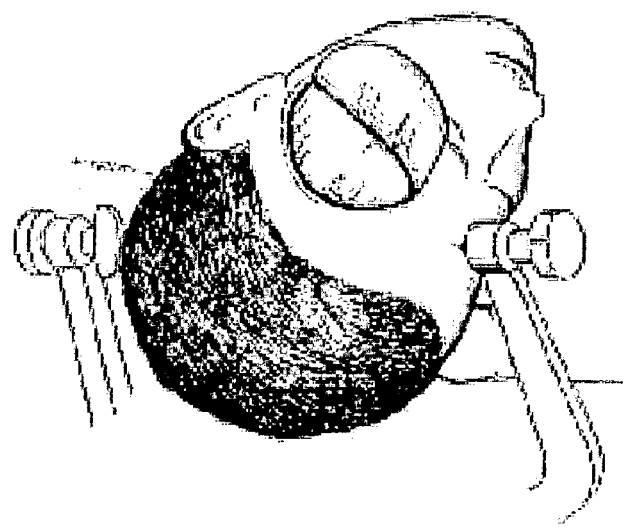
FIG. 4 illustrates a pterional incision made to expose the temporalis muscle and skull in the patient of FIG. 3.
Figure 5:
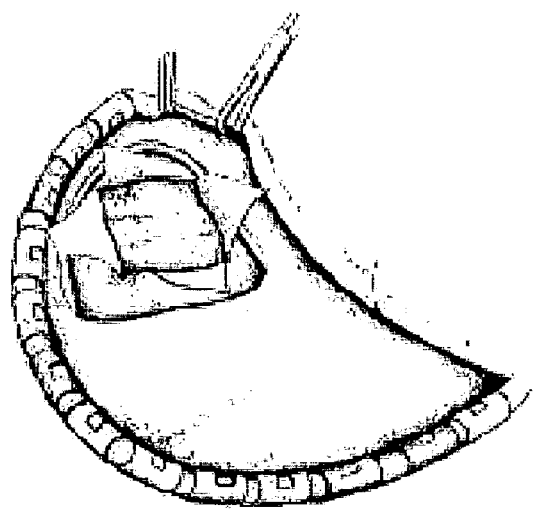
FIG. 5 illustrates a close up of the incisional area of FIG. 4 showing retraction of the muscle and performance of a small craniotomy, so that the dura is opened to expose the temporal tip and a small portion of the suprasylvian cortex.
Figure 6:
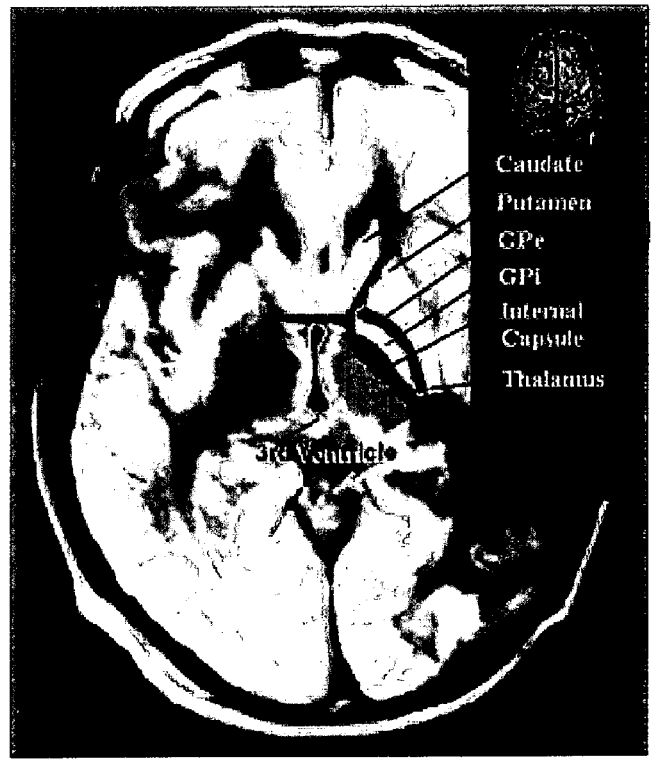
FIG. 6 is an axial MRI image through the basal ganglia showing (highlighted) in the basal ganglia, the caudate and putamen, globus pallidus externus ("Gpe"), globus pallidus internus ("Gpi") and the thalamus (inside the internal capsule and lateral to the third ventricle).

It is determined that the electrode is correctly positioned at the physiologic target site, as the mere presence of the electrode in Vim, and/or high frequency stimulation causes a reduction in the epileptic tremor. In addition, stimulation is also used to ensure that there is no evidence or neurologic impairment with particular attention being paid to speech and motor difficulties. The FIG. 6 MRI image shows the general location of the thalamus (further delineated by FIG. 7). The optic tract is avoided to prevent vision deficits.

Once the target has been confirmed, a test infusion of 1 μl of 0.1 Unit a botulinum toxin type A in non-preserved saline is made. During this time, the patient is tested neurologically for contralateral motor dexterity and sensation along with verbal skills. As there no seizure induced and no neurologic problems noted, a further infusion of 2 μl of 0.2 Units of the toxin is carried out. During the toxin infusion the neurological status of the patient is continuously monitored and infusion is halted if any impairment or change is noted. If complete abolition of the tremor has not been accomplished, then the infusion volume is increased as guided by the intraoperative physiologic responses and recordings.

After toxin infusion, the electrode and it's accompanying catheter is withdrawn, and the incision is irrigated. The burr hole is filled with Gelfoam and bone dust and the scalp is closed using a layer of inverted 3.0 Vicryl sutures for the galea and 4.0 nylon for the skin. The frame is removed and a dry sterile dressing is placed.

Bilateral toxin induced thalamotomies are generally associated with a high complication rate and not undertaken.

After a brief period of observation the patient is returned directly to his room. The patient continues with his preoperative medications and outside of mild analgesics, no other medications are given. Given that hemorrhage is an important cause of serious morbidity, good control of blood pressure in the perioperative period is maintained. An MRI scan is obtained within the first 24 hours to assess toxin location and to exclude perioperative complications. If neurologically stable, the patient is discharged on the first postoperative day. Sutures are removed one week after surgery. A short course of outpatient rehabilitation therapy is provided to optimize functional recovery of the affected limb. The intracranial botulinum toxin therapy cures the patient as he remains free of any epileptic seizures for between six months and five years.

Example 12

Treatment of Epilepsy by Administration of a Botulinum Toxin to an Epileptogenic Focus Located in the Globus Pallidus Patient DE, a 49 year old male is evaluated for pallidotomy through an extensive preoperative assessment. Before surgery, the patient is kept without medications for 12 hours. This is done to ensure that patient is in his OFF state in order to minimize involuntary movements during imaging and to more readily assess the effects of surgery. Prior to placement of the frame the patient is mildly sedated with a short acting sedative, such as midazolam or propofol.

Pallidotomy is performed under local anesthesia and requires the full cooperation of the patient therefore the intraoperative use of sedating agents is avoided. Intravenous access is established ipsilateral to the planned pallidotomy to allow complete freedom of movement in the extremity of interest and oxygen is supplied by nasal cannula. EKG, pulse oximetry and BP is monitored but an arterial line is not inserted. Blood pressure is maintained in the normal range for the patient. Bladder catheterization is not performed. An MRI compatible CRW stereotactic frame is then affixed to the cranial vault after infiltration of the pin insertion sites with 1% lidocaine with 1/200,000 epinephrine. Attention is directed to insure that the frame is not tilted or skewed for optimal imaging and target localization. The patient is then brought to the MRI scanner.

A mid-sagittal T1 weighted scout is obtained. This image is used to align the gantry of the scanner so that axial images are parallel to the AC-PC (anterior commissure-posterior commissure) plane. Next T1 weighted (TR 400, TE 12/Fr, FOV 30×30, 2 NEX, 3 mm thickness) axial images are obtained through the basal ganglia. The patient is then taken to the CT scanner and after the appropriate localizer is placed, axial CT images (DFOV, 1.5 mm thickness) through the area of interest are obtained. An alternative imaging strategy involves first obtaining T1 weighted sagittal images followed by fast spin echo inversion recovery axial and coronal images. This sequence is better delineates gray/white matter differences and allows for better visualization of the internal capsule and optic tract. Another imaging the strategy is to use a 3 dimensional SPGR volumetric sequence but these series generally require 10-11 minutes and are thus subject to movement artifacts. These images permit reconstruction of the images in sagittal, coronal and axial planes with 0.75-1.5 mm slice thickness.

The selected pallidal target based upon the location of the identified focal epileptogenic nucleus lies 2-3 mm in front of the mid-commissural point, 5-6 mm below the intercommissural line, and 19-22 mm lateral to the midline of the third ventricle. The appropriate coordinates are obtained from both the MRI and CT images and are compared for accuracy. A correctly placed toxin infusion will lie just behind the posterior margin of the mammilary bodies and just superior and lateral to the optic tract on the appropriate images.

Once the imaging is complete, the patient is brought to the operating room. A single dose of an appropriate prophylactic antibiotic (typically cefazolin) is given. The patient is placed in a supine semi-sitting position, with the head slightly raised above the horizontal, and the frame is affixed to the table. The head of the table is not be excessively elevated so as to prevent air embolism. Great care is taken to insure that the patient are comfortable since his cooperation is necessary for a successful procedure. A grounding patch is attached to the patient to allow for stimulation and toxin lesioning. A small patch of hair is shaved over the appropriate frontal region and the area is then prepared and draped. Draping is kept to a reasonable minimum to allow for intraoperative assessment of the patient. A single clear plastic drape is placed over the patient's head.

The skin is infiltrated with 1% lidocaine with 1/200,000 epinephrine. A 2.5 cm parasagittal incision is made centered at a point about 3 cm lateral to the midline, in the midpupillary line, and 1-2 cm anterior to the coronal suture. A Hudson brace is used to make a 1 cm burr hole and the bone edges are waxed. The dura is coagulated and opened. Next, the pia of the underlying cortex is coagulated with the bipolar, and a small pial incision is made to allow for atraumatic introduction of the electrode. At this point the stereotactic frame is brought into position and the electrode guide is lowered into the burr hole. The trajectory of the electrode subtends an angle of 65-70 degrees from the horizontal and 5-10 degrees from the sagittal planes. A piece of Gelfoam is placed around the guide tube and the skin is temporarily closed over the hole with nylon sutures to prevent excessive loss of CSF and brain settling.

Microelectrode recordings are made to better identify the optimal toxin infusion location and to minimize the risk of injury to the internal capsule or the optic tract. The techniques for microelectrode recording in the globus pallidus have been well described by Lozano et al (Lozano A, et al., *Methods for microelectrode guided posteroventral pallidotomy*, J Neurosurg 1996; 84:194-202). Tungsten microelectrodes with an impedance of 1-2 M Ohm at 1 khz are used.

The electrodes are clamped to the stereotactic frame and advanced through a guide tube with a microdrive. The microelectrode is connected via short leads to a preamplifier which increases the signal to noise ratio. The leads from the electrode to the preamplifier are kept short to minimize the introduction of background electrical noise. The signal from the preamplifier is then filtered, amplified, and passed through a window discriminator. The window discriminator is an electronic device which converts action potentials to digital pulses. These digital pulses are stored and analyzed off-line. In addition, the pulses can be converted to an audio signal which is useful for listening to the activity of cells without interference from background neuronal noise.

During pallidotomy, recordings proceed from the putamen and Gpe through the Gpi and then near the optic tract. Once the electrode emerges from the ventral border of the GP into the white matter of the ansa lenticularis, neuronal activity diminishes along with background activity. Deeper penetration of 1-2 mm places the electrode tip in close proximity to or within the optic tract. It is difficult to record directly from the optic tract because it contains only axons and the action potentials are correspondingly small. Photic stimulation with averaging of the evoked visual potential is therefore used. Proximity to the optic tract is determined by microstimulation as follows. A 1 sec train consisting of 2 msec square wave pulses at 300 Hz is used to elicit visual phenomenon. Visual thresholds at or near the optic tract are usually between 2-20 æA. The patient report seeing flashing lights of various colors or scotomata in the contralateral visual field.

Macrostimulation is also used to verify the location of the site for toxin infusion. Impedance monitoring, stimulation, but not lesioning, are handled by a Radionics RF lesion generator. A macroelecrode with a 2×1.6 mm uninsulated tip is introduced through the guide tube under impedance monitoring. The impedance is seen to drop about 100 when the gray matter of the basal ganglia is reached. The electrode is stopped at a point 6 mm above the target and macrostimulation is then used to further delineate the optimal target location. Low frequency stimulation is performed with square wave pulses at a frequency of 2 Hz at 0-5 Volts to obtain motor thresholds in order to insure that the lesion does not injure the internal capsule. High frequency stimulation using square wave pulses of 50-75 Hz at 0-5 Volts is used to assess for proximity to the optic tract, speech dysfunction, and amelioration of symptoms. Stimulation is carried out at 6 mm, 4 mm, and 2 mm above the target and at the target. At each point both low and high frequency stimulation is performed. To obtain the motor thresholds, low frequency stimulation is used and the voltage is gradually increased until fine contractions can be seen in the contralateral hand and/or the tongue. The voltage at which definite contractions can be first seen is the motor threshold. As the electrode is lowered the thresholds are seen to decrease. The motor thresholds are around 4-5 volts at the highest electrode position and decrease to about 2-3 volts at the target. When the electrode is near the target it is usually wise to perform high frequency stimulation first to insure that the electrode is not too close to the optic tract before proceeding with low frequency stimulation. Once the electrode is 2 mm above target, visual thresholds are obtained by turning off the room lights and asking the patient to report if he sees any flashing lights as the voltage as quickly increased and decreased with the high frequency stimulation. The classical response is a perception of flashing lights or phosphenes in the contralateral hemifield. The minimal voltage which elicits visual phenomenon constitutes the visual threshold. The electrode is then lowered to the target position and visual thresholds are again assessed. Correct placement of the electrode is determined by visual thresholds between 2-3 volts.

Once the target location is verified A botulinum toxin type A can be injected into the target tissue through a stereotactically placed 30 gauge stainless steel tube using the method set forth by Levy R., et al., *Lidocaine and muscimol microinjections in subthalamic nucleus reverse parkinsonian symptoms*, Brain (2001), 124, 2105-2118. Thus, the injection cannula can be connected to a 10-15 cm piece of polyethylene tubing with a inside diameter of 0.58 mm and sealed with epoxy glue. The aqueous toxin can be preloaded in the cannula and polyethylene tubing.

After toxin infusion the patient is then assessed for any evidence of motor, sensory, visual, or speech impairment. If there are no deficits, the full complement of toxin is infused. With careful attention to detail the technique described above can be reliably used to create a toxin induced lesions in the posteroventral pallidum. Typically, these acute lesions are about 100-150 cu mm and shrink over time.

At the completion of surgery the patient is allowed to take his next scheduled medication. After a brief period of observation, the patient is returned directly to his room. An MRI scan is obtained within the first 24 hours to assess lesion location and to rule out unforeseen complications. The patient continues with his preoperative medications and outside of mild analgesics, no other medications are necessary. The intracranial botulinum toxin therapy cures the patient as he remains free of any epileptic seizures for between six months and five years.

Example 13

Treatment of Epilepsy by Administration of a
Botulinum Toxin to an Epileptogenic Focus
Located in the Left Hippocampus The methodology set forth in Example 11 can be carried out to treat mesial temporal lobe epilepsy wherein the identified epileptogenic focus is located in the left hippocampus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x −20, y −21, z −16. This intracranial botulinum toxin therapy can cure the patient as he remains free of any epileptic seizures for between six months and five years.

Example 14

Treatment of Epilepsy by Administration of a
Botulinum Toxin to an Epileptogenic Focus
Located in the Left Middle Temporal Gyrus The methodology set forth in Example 11 can be carried out to treat mesial temporal lobe epilepsy wherein the identified epileptogenic focus is located in the left middle temporal gyrus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x −52, y −19, z −10. This intracranial botulinum toxin therapy can cure the patient as he remains free of any epileptic seizures for between six months and five years.

Example 15

Treatment of Epilepsy by Administration of a Botulinum Toxin to an Epileptogenic Focus Located in the Left Fusiform Gyrus The methodology set forth in Example 11 can be carried out to treat mesial temporal lobe epilepsy wherein the identified epileptogenic focus is located in the left fusiform gyrus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x −47, y −42, z −16. This intracranial botulinum toxin therapy can cure the patient as he remains free of any epileptic seizures for between six months and five years.

Example 16

Treatment of Epilepsy by Administration of a Botulinum Toxin to an Epileptogenic Focus Located in the Right Hippocampus The methodology set forth in Example 11 can be carried out to treat mesial temporal lobe epilepsy wherein the identified epileptogenic focus is located in the right hippocampus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x +29, y −18, z −16. This intracranial botulinum toxin therapy can cure the patient as he remains free of any epileptic seizures for between six months and five years.

Example 17

Treatment of Epilepsy by Administration of a Botulinum Toxin to an Epileptogenic Focus Located in the Right Middle Temporal Gyrus The methodology set forth in Example 11 can be carried out to treat mesial temporal lobe epilepsy wherein the identified epileptogenic focus is located in the right middle temporal gyrus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x +59, y −22, z −4. This intracranial botulinum toxin therapy can cure the patient as he remains free of any epileptic seizures for between six months and five years.

Example 18

Treatment of Epilepsy by Administration of a Botulinum Toxin to an Epileptogenic Focus Located in the Right Superior Temporal Gyrus The methodology set forth in Example 11 can be carried out to treat mesial temporal lobe epilepsy wherein the identified epileptogenic focus is located in the right superior temporal gyrus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x +64, y −27, z +11. This intracranial botulinum toxin therapy can cure the patient as he remains free of any epileptic seizures for between six months and five years.

Example 19

Treatment of Epilepsy by Administration of a Botulinum Toxin to an Epileptogenic Focus Located in the Right Fusiform Gyrus The methodology set forth in Example 11 can be carried out to treat mesial temporal lobe epilepsy wherein the identified epileptogenic focus is located in the right fusiform gyrus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x +44, y −57, z −16. This intracranial botulinum toxin therapy can cure the patient as he remains free of any epileptic seizures for between six months and five years.

Example 20

Treatment of Epilepsy by Administration of a Botulinum Toxin to an Epileptogenic Focus Located in the Right Mesial Frontal Gyrus The methodology set forth in Example 11 can be carried out to treat mesial temporal lobe epilepsy wherein the identified epileptogenic focus is located in the right mesial frontal gyrus region of the brain by administering the botulinum toxin to the following stereotactic coordinates (in mm) (where the center of gravity is determined according to Talairach J., et al., *Co-Planar Stereotactic Atlas of the Human Brain. 3-Dimensional proportional system: an approach to cerebral imaging*. Theime Verlag, Stuttgart, New York (1988)): x +10, y +41, z +14. This intracranial botulinum toxin therapy can cure the patient as he remains free of any epileptic seizures for between six months and five years.

The Examples above show that method within the scope of the claims can be used to successfully treat epilepsy in humans regardless of the particular type or origin of the epilepsy. The invention therefore provides a treatment for many different types of epilepsy.

Methods according to the present invention can also be used diverse movement disorders, including essential tremor, multiple sclerosis related tremors, post traumatic tremors, post hemiplegic tremors, parkinsonian tremors and epilepsy.

An intracranial neurotoxin administration method for treating a movement disorder according to the invention disclosed herein for has many benefits and advantages, including the following:

1. the symptoms of a movement disorder can be dramatically reduced.

2. the symptoms of a movement disorder can be reduced for from about two to about four months per injection of neurotoxin and for from about one year to about five years upon use of a controlled release neurotoxin implant.

3. the injected or implanted neurotoxin exerts an intracranial target tissue site specific tremor suppressant effect.

4. the injected or implanted neurotoxin shows little or no tendency to diffuse or to be transported away from the intracranial injection or implantation site.

5. few or no significant undesirable side effects occur from intracranial injection or implantation of the neurotoxin.

6. the amount of neurotoxin injected intracranially can be considerably less than the amount of the same neurotoxin required by other routes of administration (i.e. intramuscular, intrasphincter, oral or parenteral) to achieve a comparable tremor suppressant effect.

7. the tremor suppressant effects of the present methods can result in the desirable side effects of greater patient mobility, a more positive attitude, and an improved quality of life.

8. high, therapeutic doses of a neurotoxin can be delivered to an intracranial target tissue over a prolonged period without systemic toxicity.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes intracranial administration methods wherein two or more neurotoxins, such as two or more botulinum toxins, are administered concurrently or consecutively. For example, botulinum toxin type A can be administered intracranially until a loss of clinical response or neutralizing antibodies develop, followed by administration of botulinum toxin type B. Alternately, a combination of any two or more of the botulinum serotypes A-G can be intracranially administered to control the onset and duration of the desired therapeutic result. Furthermore, non-neurotoxin compounds can be intracranially administered prior to, concurrently with or subsequent to administration of the neurotoxin to proved adjunct effect such as enhanced or a more rapid onset of tremor suppression before the neurotoxin, such as a botulinum toxin, begins to exert its more long lasting tremor suppressant effect.

Our invention also includes within its scope the use of a neurotoxin, such as a botulinum toxin, in the preparation of a medicament for the treatment of a movement disorder, by intracranial administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method for treating focal epilepsy, the method comprising the step of intracranial administration of a botulinum toxin into intracranial target tissue having an epileptogenic focus located at a brain region selected from the group consisting of a lower brain region, a pontine region, a globus pallidus and a thalamus of a patient, thereby treating the focal epilepsy.

2. The method of claim 1, wherein the botulinum toxin is selected from the group consisting of botulinum toxin types A, B, C, D, E, F and G.

3. The method of claim 1, wherein the botulinum toxin is botulinum toxin type A.

4. The method of claim 1, wherein the botulinum toxin is administered in an amount of between about $10^{-3}$ U/kg and about 100 U/kg of patient weight.

5. The method of claim 1, wherein the method alleviates epilepsy for between about 1 month and about 5 years.

6. The method of claim 1, wherein the intracranial administration step comprises implantation of a controlled release botulinum toxin system.

7. A method for treating focal epilepsy, the method comprising the step of intracranial administration of a therapeutically effective amount of a botulinum toxin type A into intracranial target tissue having an epileptogenic focus located at a temporal lobe of a patient, thereby treating the focal epilepsy.

8. A method for treating a focal epilepsy, the method comprising the step of intracranial administration of a therapeutically effective amount of a botulinum toxin type to a epileptogenic focus of a patient located in a thalamus of a patient between 3 to 6 mm posterior to the mid anterior commissure-posterior commissure plane, 12 mm to 16 mm lateral to the mid anterior commissure-posterior commissure plane, and 0 to 3 mm above the level of the mid anterior commissure-posterior commissure plane, thereby treating the focal epilepsy.

9. A method for treating focal epilepsy, the method comprising the step of intracranial administration of 1-10 units of botulinum toxin type A to into intracranial target tissue having an epileptogenic focus located at a brain region selected from the group consisting of a lower brain region, a pontine region, a globus pallidus and a thalamus of a patient, thereby treating the focal epilepsy.

10. A method for treating epilepsy having an epileptogenic focus, the method comprising the step of intracranial administration of a botulinum toxin into intracranial target tissue having an epileptogenic focus located at a brain region selected from the group consisting of a temporal lobe and a thalamus of a patient, thereby treating the epilepsy.

11. The method of claim 10, wherein the botulinum toxin is selected from the group consisting of botulinum toxin types A, B, C, D, E, F and G.

12. The method of claim 10, wherein the botulinum toxin is botulinum toxin type A.

13. A method for treating epilepsy having an epileptogenic focus, the method comprising the step of intracranial administration of 1-10 units of a botulinum toxin into intracranial target tissue having an epileptogenic focus located at a brain region selected from the group consisting of a lower brain region, a pontine region, a globus pallidus and a thalamus of a patient, thereby treating the epilepsy.

14. A method for treating focal epilepsy, the method comprising the step of intracranial administration of a botulinum toxin into intracranial target tissue having an epileptogenic focus located at a hippocampus of a patient, thereby treating the focal epilepsy.

15. The method of claim 14, wherein the botulinum toxin is selected from the group consisting of botulinum toxin types A, B, C, D, E, F and G.

16. The method of claim 14, wherein the botulinum toxin is botulinum toxin type A.

17. The method of claim 14, wherein intracranial administration is performed subsequent to a step of utilizing stereotactic surgical procedures to identify the epileptogenic focus.

18. A method for treating focal epilepsy, the method comprising the step of intracranial administration of a botulinum toxin into intracranial target tissue having an epileptogenic focus located at a frontal lobe of a patient, thereby treating the focal epilepsy.

19. The method of claim 18, wherein the botulinum toxin is selected from the group consisting of botulinum toxin types A, B, C, D, E, F and G.

* * * * *

UNITED STATES PATENT AND TRADEMARK OFFICE
CERTIFICATE OF CORRECTION

PATENT NO. : 7,357,934 B2
APPLICATION NO. : 10/421504
DATED : April 15, 2008
INVENTOR(S) : Donovan et al.

It is certified that error appears in the above-identified patent and that said Letters Patent is hereby corrected as shown below:

On the Title Page Item -56-, under "Other Publications", line 14, delete "Phsyiology" and insert -- Physiology --, therefor.

On the Title Page Item -56-, under "Other Publications", line 21, delete "Nuerol" and insert -- Neurol --, therefor.

On the Title Page Item -56-, under "Other Publications", line 21, delete "Suup" and insert -- Suppl --, therefor.

On the Title Page Item -56-, under "Other Publications", line 35, delete "Expermental" and insert -- Experimental --, therefor.

On the Title Page Item -56-, under "Other Publications", line 48, delete "Neurotixins" and insert -- Neurotoxins --, therefor.

On the Title Page Item -56-, under "Other Publications", line 33, delete "transaction" and insert -- transection --, therefor.

On the Title Page Item -56-, under "Other Publications", line 73, delete "2073-207" and insert -- 2073-2076 --, therefor.

On the Title Page Item -56-, under "Other Publications", line 3, delete "290" and insert -- 280 --, therefor.

On the Title Page Item -56-, under "Other Publications", line 40, delete "Acetycholine" and insert -- Acetylcholine --, therefor.

On the Title Page Item -56-, under "Other Publications", line 4, after "Richard" delete "r." and insert -- R. --, therefor.

In column 1, line 45, after "interest has" delete "be" and insert -- been --, therefor.

In column 4, line 60, delete "orphenedrine" and insert -- orphenadrine --, therefor.

In column 5, line 29, before "Shorvon" delete "(".

In column 6, line 12, after "editors" delete ")".

In column 9, line 7, before "selective" delete "(".

In column 9, line 20, after "2002" delete ")".

UNITED STATES PATENT AND TRADEMARK OFFICE
CERTIFICATE OF CORRECTION

PATENT NO. : 7,357,934 B2
APPLICATION NO. : 10/421504
DATED : April 15, 2008
INVENTOR(S) : Donovan et al.

It is certified that error appears in the above-identified patent and that said Letters Patent is hereby corrected as shown below:

In column 10, lines 63-64, after "2001)." delete "new approach to the surgical treatment of focal epilepsy, J Neurosurg 70: 231-239:1989)" and insert the same at Col. 11, Line 6 after "transection: a" as a continuation of the paragraph.

In column 11, lines 6-8, after "transection: a" delete "The MST procedure physically disrupts these horizontal interconnections while sparing the vertically-oriented cortical function".

In column 11, line 23, delete "ocus" and insert -- focus --, therefor.

In column 13, line 18, delete "LD50" and insert -- $LD_{50}$ --, therefor.

In column 13, line 28, delete "chapte r" and insert -- chapter --, therefor.

In column 13, line 30, delete "LD50" and insert -- $LD_{50}$ --, therefor.

In column 13, line 34, delete "LD50" and insert -- $LD_{50}$ --, therefor.

In column 15, line 6, delete "hemaglutinin" and insert -- hemagglutinin --, therefor.

In column 15, lines 6-7, delete "nonhemaglutinin" and insert -- nonhemagglutinin --, therefor.

In column 15, line 53, after "use" delete ")".

In column 15, line 54, delete "haemagglutinin" and insert -- hemagglutinin --, therefor.

In column 15, line 58, after "use" delete ")".

In column 16, line 34, after "1987" insert --)--.

In column 18, line 14, delete "reconstitued" and insert -- reconstituted --, therefor.

In column 19, line 15, delete "puboreetalis" and insert -- puborectalis --, therefor.

In column 19, line 19, delete "Lid" and insert -- lid --, therefor.

In column 19, line 23, after "complex)" insert -- , --.

In column 19, line 32, delete "sublimus" and insert -- sublimis --, therefor.

In column 19, line 35, delete "brachui" and insert -- brachii --, therefor.

UNITED STATES PATENT AND TRADEMARK OFFICE
CERTIFICATE OF CORRECTION

PATENT NO. : 7,357,934 B2
APPLICATION NO. : 10/421504
DATED : April 15, 2008
INVENTOR(S) : Donovan et al.

It is certified that error appears in the above-identified patent and that said Letters Patent is hereby corrected as shown below:

In column 23, line 67, after "1999" insert -- . --.

In column 24, line 44, after "proteins" insert -- . --.

In column 25, line 3, after "metabolism" insert --. --.

In column 25, line 37, after "spasticity" insert -- . --.

In column 28, line 15, delete "1988" and insert -- 1998--, therefor.

In column 28, line 32, delete "trafficking:" and insert -- trafficking,: --, therefor.

In column 28, line 53, Before "Huttner" delete "(".

In column 29, line 21, after "into" delete "a" and insert -- an --, therefor.

In column 30, line 28, after "Ohio" delete "," and insert -- ) --, therefor.

In column 30, line 40, delete "Inrraoperative" and insert -- Intraoperative --, therefor.

In column 35, line 64, after "preparation" insert -- ) --.

In column 40, line 3, delete "epinephrine he" and insert -- epinephrine. The --, therefor.

In column 46, line 5, after "tubing with" delete "a" and insert -- an --, therefor.

Signed and Sealed this

Eighth Day of July, 2008

JON W. DUDAS
*Director of the United States Patent and Trademark Office*